(12) United States Patent
Cohen et al.

(10) Patent No.: US 11,439,727 B2
(45) Date of Patent: Sep. 13, 2022

(54) 3D PRINTABLE BIO GEL AND METHOD OF USE

(71) Applicant: TDBT IP INC., New York, NY (US)

(72) Inventors: Daniel L. Cohen, Brooklyn, NY (US); Chris Pelletier, Watkins Glen, NY (US)

(73) Assignee: TDBT IP INC., New York, NY (US)

( * ) Notice: Subject to any disclaimer, the term of this patent is extended or adjusted under 35 U.S.C. 154(b) by 273 days.

(21) Appl. No.: 16/304,212

(22) PCT Filed: May 25, 2017

(86) PCT No.: PCT/US2017/034582
§ 371 (c)(1),
(2) Date: Nov. 23, 2018

(87) PCT Pub. No.: WO2017/205695
PCT Pub. Date: Nov. 30, 2017

(65) Prior Publication Data
US 2020/0316252 A1 Oct. 8, 2020

Related U.S. Application Data

(60) Provisional application No. 62/341,960, filed on May 26, 2016.

(51) Int. Cl.
| | |
|---|---|
| *A61L 27/24* | (2006.01) |
| *A61L 27/38* | (2006.01) |
| *A61L 27/52* | (2006.01) |
| *B33Y 10/00* | (2015.01) |
| *B33Y 70/00* | (2020.01) |
| *A61L 27/54* | (2006.01) |

(52) U.S. Cl.
CPC ........... *A61L 27/24* (2013.01); *A61L 27/3804* (2013.01); *A61L 27/52* (2013.01); *A61L 27/54* (2013.01); *B33Y 10/00* (2014.12); *B33Y 70/00* (2014.12)

(58) Field of Classification Search
CPC .................................. A61L 27/52; A61L 11/20
See application file for complete search history.

(56) References Cited

U.S. PATENT DOCUMENTS

| | | | |
|---|---|---|---|
| 4,066,083 A | 1/1978 | Ries | |
| 5,106,949 A * | 4/1992 | Kemp | C07K 14/78 530/356 |
| 2006/0135921 A1* | 6/2006 | Wiercinski | C08J 3/12 604/368 |
| 2018/0339455 A1 | 11/2018 | Cohen et al. | |

FOREIGN PATENT DOCUMENTS

| | | |
|---|---|---|
| EP | 0 419 111 A1 | 3/1991 |
| EP | 1 856 272 | 11/2007 |
| WO | WO-00/29484 A1 | 5/2000 |
| WO | WO-20 1 5/084972 | 6/2015 |

OTHER PUBLICATIONS 3D printable storage modulus—Google scholar search—Nov. 21, 2020 (Year: 2020).*
L.M. Delgado, Y. Bayon, A. Pandit, and D.I. Zeugolis. To Cross-Link or not to Cross-Link? Cross-Linking Associated Foreign Body Response of Collagen-Based Devices. Tissue Engineering: Part B vol. 21, No. 3, 2015298-313. (Year: 2015).*
A.K. Sommer. ("Better teeth and fewer wrinkles: Israeli technology puts collagen to work." Downloaded May 3, 2021 from https:// www.israel21c.org/better-teeth-and-fewer-wrinkles-israeli-technology-putscollagen-to-work/. Available on the Internet Apr. 10, 2005. (Year: 2005).*
D. L. Cohen, W. Lo, A. Tsavaris, D. Peng, H. Lipson, and L. J. Bonas. "Increased Mixing Improves Hydrogel Homogeneity and Quality of Three-Dimensional Printed Constructs," Tissue Engineering: Part C, vol. 17, No. 2, 2011, 239-248. (Year: 2011).*
Google_scholar_search_11-12-21_daniel_cohen_3d_printing_homogeneity (Year: 2021).*
International Search Report for PCT/US2017/034582 dated Oct. 24, 2017 (5 pages).
Lin et al., "Low-Temperature Additive Manufacturing of Biomimic Three-Dimensional Hydroxyapatite/Collagen Scaffolds for Bone regeneration", ACS Appl. Mater. Interfaces, 2016, vol. 8, No. 11, pp. 6905-6916.
Rhee et al., "3D Biopringing of Spatially Heterogeneous Collagen Constructs for Cartilage Tissue Engineering", ACS Biomaterials Science & Engineering, 2016, vol. 2, No. 10, pp. 1800-1805.
Vivian K Lee et al., "Creating perfused functional vascular channels using 3D bio-printing technology", Biomaterials, 2014, vol. 35, No. 2, pp. 8092-8102.
Office Action in Chinese Patent Application CN 201780046992.3 dated May 14, 2021.
Office Action in Japanese Patent Application JP 2019-514192 dated Jun. 1, 2021.

* cited by examiner

*Primary Examiner* — Michael P Cohen
(74) *Attorney, Agent, or Firm* — Sunit Talapatra; Foley & Lardner, LLP

(57) ABSTRACT

Collagen compositions, methods for preparing those collagen compositions, and 3D constructs formed from those collagen compositions are provided. In particular, methods of isolating collagen that exhibits an enhanced rate of gelling, such collagen compositions, and 3D constructs formed from such collagen compositions are provided.

20 Claims, 11 Drawing Sheets

METHOD OF PREPARING 3D STRUCTURE FROM BIO GEL

METHOD OF PREPARING BIO GEL COMPOSITIONS FOR 3D STRUCTURE FABRICATION

3D PRINTABLE BIO GEL AND METHOD OF USE

CROSS-REFERENCE TO RELATED PATENT APPLICATIONS

This application claims the benefit of and priority to U.S. Provisional Application No. 62/341,960 filed May 26, 2016, which is incorporated herein by reference in its entirety.

BACKGROUND

The present technology relates generally to 3D-printable bio gels. More particularly, the present technology relates to methods and compositions of collagen-containing 3D printable bio gels for use in fabricating three-dimensional structures thereof.

Given their broad application, collagen-based materials could prove to be advantageous substrates for use in 3D printing technology. The structure, function, and properties of collagen make it an important material for a myriad number of tissue engineering purposes. Currently available collagens reflect its diverse capabilities; yet, available collagen processes yield formulations with unfavorable properties (e.g., gelation rate, strength, elasticity, and rheology). Certain 3D manufacturing processes e.g., additive manufacturing, require biomaterials with rapid gelation properties which can be challenging to achieve in bio-based materials.

The present technology is directed to overcoming these and other deficiencies.

SUMMARY OF THE INVENTION

One aspect of the present technology relates to a method of harvesting collagen. The method includes processing a collagen-based biomaterial to obtain biomaterial particles. In some embodiments, the collagen-based biomaterial is type I collagen derived from a mammalian source. In some embodiments, the method includes contacting the biomaterial particles with a weak acid solution to obtain a collagen-containing solution. In some embodiments, the method includes segregating the collagen-containing solution. In some embodiments, the segregating includes centrifugation. In some embodiments, the method includes contacting the collagen-containing solution with a salt solution to obtain a collagen precipitate. In some embodiments, the method includes re-suspending the collagen precipitate to obtain a re-suspended collagen solution. In some embodiments, the method optionally includes performing viral and prion inactivation of the re-suspended collagen solution. In some embodiments, the method includes desalting the re-suspended collagen solution. In some embodiments, the method includes drying the re-suspended collagen solution to obtain a collagen material. In some embodiments, the method includes sterilizing the collagen material.

In another aspect, the present technology provides a bio gel composition. The bio gel composition includes a collagen material harvested as described above. In some embodiments, the bio gel composition may include collagen material in a weak acid solution. In some embodiments, the bio gel composition may be prepared using suitable amounts of collagen material. In some embodiments, the bio gel composition may include collagen material in an amount greater than 5 mg/mL. In some embodiments, the bio gel composition may undergo rapid gelation at room temperature or greater. In some embodiments, the bio gel composition of the present technology may also be liquid under a shear stress of 15 Pa to 100 Pa before gelation and remains solid under a hydrostatic pressure of about 30 Pa to about 120 Pa during gelation. In some embodiments, the bio gel composition includes carriers and non-natural additives, such as cross-linking agents.

In another aspect, the present technology provides a method of preparing a three-dimensional structure from the bio gel composition described in this application. In some embodiments, the method includes providing a bio gel composition to a modular fabrication system. In some embodiments, modular fabrication system is a 3D printing device. In some embodiments, the method includes maintaining the bio gel composition at a temperature of about 0° C. to about 12° C. In some embodiments, the method includes depositing the bio gel composition to form a three-dimensional structure, where the three-dimensional structure undergoes gelation. In some embodiments, the method includes curing the three-dimensional structure.

In yet another aspect, the present technology also provides a method of preparing a bio gel composition for use in three-dimensional structure fabrication. In some embodiments, the method includes providing a first receptacle having a collagen material in a weak acid solution, where the collagen material is harvested using the methods described in this application. In some embodiments, the method includes providing a second receptacle having a carrier. In some embodiments, the method may further include providing a third receptacle of living cells. In some embodiments, the method includes contacting the collagen material in weak acid solution of the first receptacle with the carrier of the second receptacle to obtain a bio gel composition having homogeneity of about 50% to about 99.9%.

DETAILED DESCRIPTION

Figure 1:
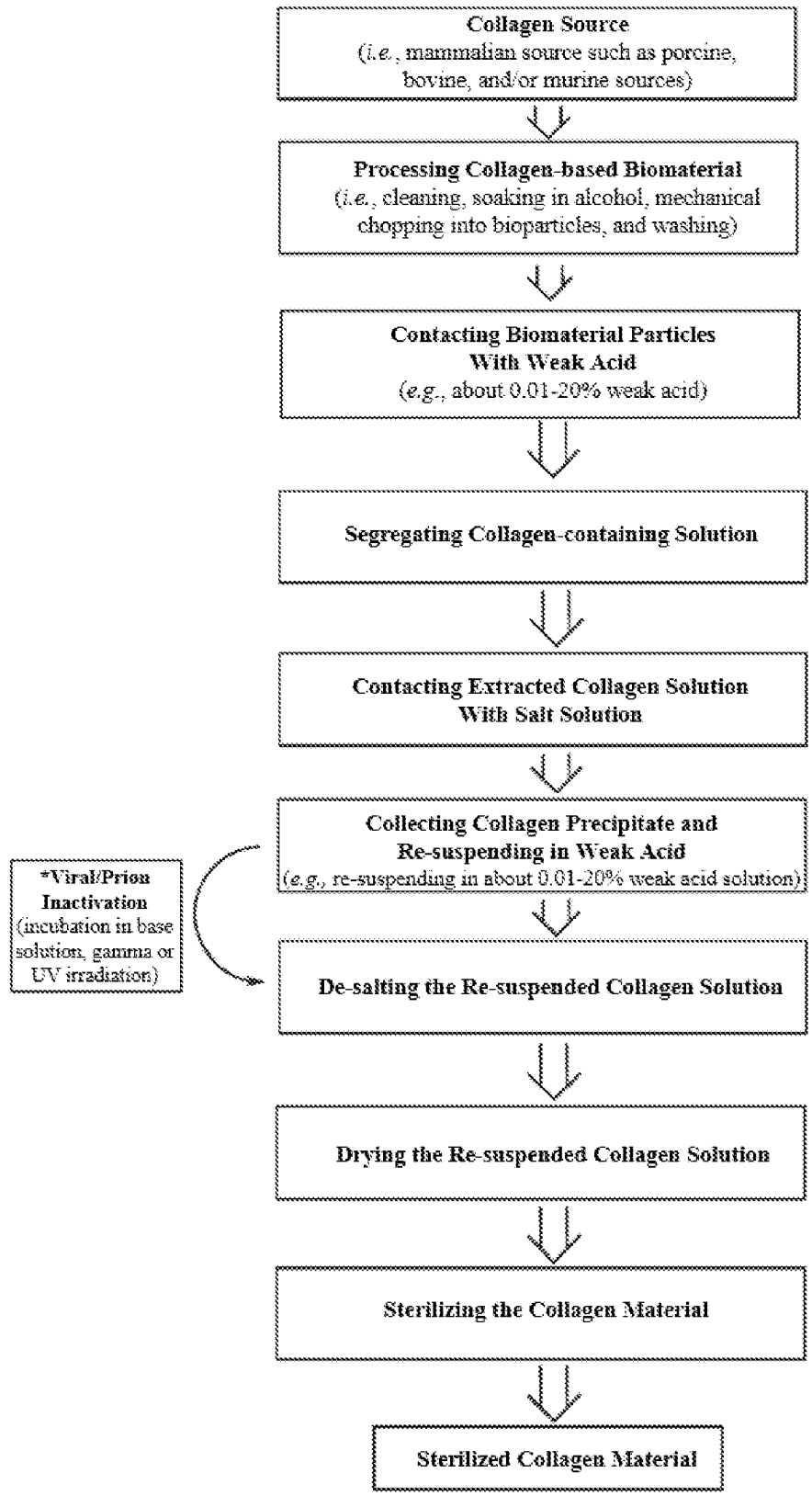
FIG. 1 is a flow chart depicting an exemplary method of the present technology for harvesting collagen.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout and are as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of refereeing individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified. The expression "comprising" means "including, but not limited to." Thus, other non-mentioned substances, additives, carriers, or steps may be present. Unless otherwise specified, "a" or "an" means one or more.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Each numerical parameter should at least be construed in light of the number reported significant digits and by applying ordinary rounding techniques. The term "about" when used before a numerical designation, e.g., temperature, time, amount, and concentration including range, indicates approximations which may vary by (+) or (−) 10%, 5% or 1%.

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

In some embodiments, the term "gel" includes, but is not limited to, non-Newtonian fluids and Bingham plastics.

As used herein, the term "shear stress" or "shear-thinning" refers to the rheological viscoelastic properties of a material related to fluid-like or non-fluid-like behavior and flow. Shear stress and shear-thinning include properties related to Bingham flow, plastic flow, pseudoplasticity, dilatancy, thixotropy, rheopexy, and the like or other stress and/or strain properties of a viscous material. Further, "shear-thinning" refers to a reduction in apparent viscosity (the ratio of shear stress to the shear rate) with increasing (pseudoplastic), time dependent (thixotropic) or associated with a yield stress, defined as a stress that must be exceeded before flow starts, (Bingham plastics and generalized Bingham plastics). See, generally, Harris, J., & Wilkinson, W. L., "Non-Newtonian Fluid," pp. 856-858 in Parker, S. P., ed., McGraw-Hill Encyclopedia of Physics, Second Edition, McGraw-Hill, New York, 1993. A suitable viscosity range of the present technology includes, but is not limited to, from 10,000 centipoise (cps) to about 30,000 cps as a resting solid, or from 3,000 cps to about 10,000 cps as liquid.

As used herein, the term "viscosity" refers to the resistance to gradual deformation by shear stress or tensile stress of a material.

As used herein, the term "peracid" refers to acids in which the OH moiety of a carboxyl group or an inorganic oxyacid, is replaced by an OOH moiety. Examples of such percarboxylic acids include, but are not limited to, performic acid and peracetic acid.

As used herein, the term "collagen" refers to the main protein of connective tissue that has a high tensile strength and that has been found in most multicellular organisms. Collagen is a major fibrous protein, and it is also the non-fibrillar protein in basement membranes. It contains an abundance of glycine, proline, hydroxyproline, and hydroxylysine. Collagen is found throughout the body, and is of at least 12 types (type I-XII).

The term "biomaterial" refers to a material derived from a natural or synthetic source.

As used herein, the term "receptacle" refers to standard systems capable of receiving and housing any materials for preparing and using the present technology as disclosed herein. Materials include, but are not limited to, collagen material, weak acid solutions, carriers, additives, solvents, living cells, cell medium, and the like or combinations thereof. For example, suitable receptacles include, but are not limited to, syringes, funnels, beakers, mixers, drums, bottles, vials, and the like.

Collagen-based materials are advantageous substrates for use as bio gels in fabricating 3D structures. In various aspects, methods of harvesting collagen for use in bio gel compositions, bio gel compositions, methods for making 3D structures using bio gel compositions, and methods for preparing bio gel compositions for use in 3D printing systems are provided.

In one aspect, disclosed herein is a method of harvesting collagen, wherein the method includes processing a collagen-based biomaterial to obtain biomaterial particles; contacting the biomaterial particles with a weak acid solution to obtain a collagen-containing solution; segregating the collagen-containing solution; contacting the collagen-containing solution with a salt solution to obtain a collagen precipitate; re-suspending the collagen precipitate to obtain a re-suspended collagen solution, and optionally, performing viral and prion inactivation of the re-suspended collagen solution; desalting the re-suspended collagen solution; drying the re-suspended collagen solution to obtain a collagen material; and sterilizing the collagen material.

The collagen-based biomaterial can be from a source, such as a vertebrate collagen source. In some embodiments, the vertebrate collagen source includes, but is not limited, mammals, birds, reptiles, fish, and the like. In some embodiments, the source is a mammalian, including but not limited to, equine, canine, porcine, bovine, feline, caprine, ovine, murine, or human. In certain embodiments, the mammalian source is porcine, bovine, murine, or a combination thereof.

In another embodiment of the present technology, the collagen-based biomaterial is from an artificial source. In certain embodiments, the artificial source includes, but is not limited to, collagen from recombinant expressed protein in cell culture, engineered cells, bacterial cell culture, mammalian cell culture, and the like or combinations thereof. In some embodiments, the artificial source is an engineered cell source. Suitable engineered cell sources include, but are not limited to, yeast cells, insect secretory cells, and the like or combinations thereof.

The collagen in the collagen-based biomaterial may be obtained from various sources including, but not limited to, tendon, skin, ligament, bone, teeth, cartilage, connective tissue, intervertebral disc, cornea, and the like and combinations thereof. In some embodiments, the collagen-based biomaterial is skin, bone, tendon, or a combination thereof. In certain embodiments, the skin, bone, or tendon may be derived from a mammalian source, including but not limited to, sources including bovine, porcine, murine, or combinations thereof. When the source is tendon, it may include, but is not limited to, common digital extensor tendon, lateral extensor tendon, deep flexor tendon, and the like or combinations thereof.

The collagen-based biomaterial may be used as such or may be subjected to quality discrimination. This discrimination may be performed using various techniques known in the art, including, but not limited to, manual visual inspection to identify areas comprising non-white surface properties or using computer vision techniques in which pixel values are read for color and intensity and regions beneath a threshold are rejected. These thresholds may include RGB values that deviate from 1:1:1 ratios by about 1%, about 5%, about 10%, about 20%, about 50%, or about 80%; and the individual channel values may be about 99%, about 95%, about 90%, about 80%, about 50%, or about 30%. In some embodiments, the discrimination includes selecting collagen-based biomaterial having less than about 5% infiltrates.

The collagen in the collagen-based biomaterial can be of any type. In some embodiments, the collagen-based biomaterial may include type I collagen. Type I collagen can be found in most connective tissues, is the most abundant collagen type in a living organism, and is found in tendons, corium, and bone. Over 90% of the collagen in the body is type I. In some embodiments the type I collagen may include insoluble collagen, collagen fibers, soluble collagen, and acid-soluble collagen. In certain embodiments, the type I collagen is soluble collagen, acid-soluble collage, or a combination thereof. In some embodiments, the type I collagen does not include atelocollagen.

In some embodiments, the present methods include processing the collagen-based biomaterial using mechanical action to obtain the biomaterial particles. Suitable mechanical action includes, but is not limited to, freezing, slicing, chopping, mincing, milling, grinding, and combinations thereof. In certain embodiments, the method may include slicing the collagen-based biomaterial into fine strands, to obtain biomaterial particles of suitable size. In one embodiment, the collagen-based biomaterial may be sliced longitudinally. In another embodiment, the slicing may be cross-longitudinal. In yet another embodiment, the slicing is both longitudinal and cross-longitudinal. In some embodiments, the slicing may be performed without freezing the collagen-based biomaterial prior to slicing. In other embodiments, the collagen-based biomaterial may be frozen to facilitate slicing. In certain embodiments, the collagen-based biomaterial is mechanically processed into biomaterial particles that have a size from about 100 μm to about 1 cm. Suitable biomaterial particle sizes include, but are not limited to, from about 100 μm to about 50 mm, about 100 μm to about 1 mm, about 100 μm to about 500 μm, about 100 μm to about 250 μm, and ranges between any two of these values or less than any one of these values.

In some embodiments, the collagen-based biomaterial further includes soaking in solvent prior to mechanical action. Suitable solvents include, but are not limited, deionized water, alcohol, or combinations thereof. Suitable alcohols include, but are not limited to, methanol, ethanol, propanol, isopropanol, and the like or combinations thereof. In some embodiments, the processing further includes washing the biomaterial particles. Washing includes adding the biomaterial particles to a buffer solution. Suitable buffer solutions include, but are not limited to, phosphate buffered saline, sodium chloride solution, phosphates, water, and phosphate buffer solution.

In some embodiments of the present technology, further to obtaining the biomaterial particles, the present method includes contacting the biomaterial particles with a weak acid solution to obtain a collagen-containing solution.

In some embodiments, the weak acid solution includes the weak acid in an amount that is about 0.01% to about 20.0% of the weak acid solution. The amount of weak acid in the weak acid solution may include, but is not limited to, about 0.01% to about 20%, about 0.01% to about 10%, about 0.01% to about 3%, about 0.1% to about 3%, about 0.3% to about 8%, about 0.5% to about 5%, about 1% to about 3%, and ranges between any two of these values or less than any one of these values. Suitable weak acid solutions include the weak acid in an amount that is about 0.01%, about 0.05%, about 0.1%, about 0.25%, about 0.5%, about 1.0%, about 1.5%, about 2.0%, about 2.5%, about 3.0%, about 4.0%, about 5.0%, about 6.0%, about 7.0%, about 8.0%, about 9.0%, about 10.0%, about 12.5%, about 15.0%, about 20% of the weak acid solution and ranges between any two of these values or less than any one of these values.

In certain embodiments of the present technology, the amount of weak acid solution contacting the biomaterial particles include, but is not limited to, about 25 mL to about 250 mL of weak acid solution per gram of biomaterial particles. Suitable amounts of weak acid solution contacting the biomaterial particles may include, but not limited to, about 25 mL/g to about 250 mL/g, about 25 mL/g to about 200 mL/g, about 25 mL/g to about 150 mL/g, about 25 mL/g to about 100 mL/g, about 25 mL/g to about 75 mL/g, about 25 mL/g to about 50 mL/g. Alternatively, suitable amounts may include about 50 mL/g to about 250 mL/g, about 100 mL/g to about 250 mL/g, about 150 mL/g to about 250 mL/g, or about 200 mg/mL to about 250 mg/mL. The amount of weak acid contacting the biomaterial particles may include, but are not limited to, about 100 mL/g, about 150 mL/g, about 200 mL/g, about 250 mg/mL and ranges between any two of these values or less than any one of these values.

The contacting of the biomaterial particles with the weak acid solution may be performed using suitable methods to ensure maximum dissolution or dispersion of the biomaterial particles in the acid solution. In some embodiments, the contacting may include, but not limited to, mixing or agitating together the biomaterial particles with the weak acid solution to obtain the collagen-containing solution. In particular embodiments, the contacting may include mixing the biomaterial particles and the weak acid solution. Suitable contacting may include manual mixing or mixing using suitable mixing equipment such as a shaker (e.g., an orbital shaker), rotator, tumbler, large tank mixer, overhead stirrer, and the like. In some embodiments, the contacting is carried out with an orbital shaker. In one embodiment, the contacting with the orbital shaker may include speeds of at least about 100 RPM to about 250 RPM, about 120 RPM to about 230 RPM, about 150 RPM to about 220 RPM, about 100 RPM to about 200 RPM, about 150 RPM to about 200 RPM, and ranges between any two of these values or less than any one of these values. In one embodiment, the contacting with the orbital shaker may include speeds of at least about 100 RPM, about 110 RPM, about 120 RPM, about 130 RPM, about 140 RPM, about 150 RPM, about 160 RPM about 170 RPM, about 180 RPM, about 190 RPM, about 200 RPM, about 210 RPM, about 220 RPM, about 230 RPM, about 240 RPM, about 250 RPM and ranges between any two of these values or less than any one of these values. In one embodiment, the orbital shaker speed is about 100 RPM to about 200 RPM. In another embodiment, the orbital shaker speed is about 100 RPM to about 150 RPM. In yet another embodiment, the orbital shaker speed is about 150 RPM to about 200 RPM.

In some embodiments, the contacting may include stirring biomaterial particles with the weak acid solution. Suitable stirring may include manual stirring, overhead stirrers, and magnetic stirrers. In some embodiments, the contacting the biomaterial particles with the weak acid solution may include a period of about 24 h to about 2 weeks. Suitable periods may include, but not limited to, about 24 h to about 10 days, about 24 h to about 7 days, about 24 h to about 5 days, about 48 h to about 14 days, about 72 h to about 9 days, about 5 days to about 14 days, about 5 days to about 7 days, and ranges between any two of these values or less than any one of these values. The period may include, but is not limited to, at least about 24 h, about 36 h, about 48 h, about 60 h, about 72 h, about 84 h, about 96 h, about 5 days, about 6 days, about 7 days, about 9 days, about 10 days, about 11 days, about 12 days, about 13 days, about 14 days and ranges between any two of these values or less than any one of these values. In one embodiment, the contacting the biomaterial particles with the weak acid solution includes periods of about 2 days to about 14 days. In another embodiment, the contacting includes periods of about 3 days to about 9 days. In yet another embodiment, the contacting includes periods of about 5 days to about 7 days.

Suitable weak acid solutions may include, but are not limited to, weak acid solutions suitable for maintaining a pH buffer between about 2.8 to about 4.0. In some embodiments, the weak acid solution maintains a pH of about 2.8 to about 4, about 2.8 to about 3.5, about 2.8 to about 3.3, about 3.0 to about 4.0, about 3.3 to about 4.0, and ranges between any two of these values or less than any one of these values. In some embodiments, suitable weak acid solutions may include, but are not limited to, solutions having a pKa of about 3 to about 7. Suitable pKa values include about 3 to about 7, about 3 to about 6, about 3 to about 5, about 3.5 to about 7, about 4 to about 7, about 4.5 to about 7, and ranges between any two of these values or less than any one of these values. Suitable weak acid solutions include, but are not limited to, formic acid, propanoic acid, acetic acid, citric acid, butanoic acid, salicylic acid, gluconic acid, heptonic acid, carbonic acid, hydrofluoric acid, nitrous acid, hypochlorous acid, hydrochloric acid, and the like or combinations thereof.

Once an acid solution of the biomaterial particles is obtained, it may be subjected to suitable processing to segregate the extracted collagen. In some embodiments of the present technology, segregating the extracted collagen from the collagen-containing solution may include, but is not limited to, centrifugation, size exclusion filtration, screen filtration, and the like or combinations thereof. In certain embodiments, the centrifugation of the collagen-containing solution may include centrifuging at a force of about 5,000 G to about 25,000 G. In certain embodiments, the centrifugation may include centrifuging at a force of about 5,000 G to about 20,000 G, about 5,000 G to about 15,000 G, about 5,000 G to about 12,000 G, and about 5,000 G to about 10,000 G. In other embodiments, the centrifugation may include centrifuging at a force of at least about 5,000 G, about 6,000 G, about 7,000 G, about 8,000 G, about 9,000 G, about 10,000 G, about 11,000 G, about 12,000 G, about 15,000 G, about 20,000 G, about 25,000 G and ranges in between any two of these values or less than any one of these values. In one embodiment, the centrifugation may include centrifuging at a force of about 9,000 G to about 12000 G.

In certain embodiments, the centrifugation may include, but is not limited to, centrifuging over a period of about 10 min to about 120 min. In certain embodiments, the periods may include, but are not limited to, 10 min to about 120 min, about 30 min to about 110 min, about 60 min to about 100 min, and ranges between any two of these values or less than any one of these values. Suitable periods may include from about 10 min, about 30 min, about 60 min, about 90 min, about 100 min, about 110 min, about 120 min, and ranges in between any two of these values or less than any one of these values. In one embodiment, the segregating may include centrifuging the collagen-containing solution over a period of about 10 min to about 90 min or about 80 min to about 110 min. In some embodiments, the segregating may include collecting the resulting supernatant solution after centrifugation.

The supernatant solution, which contains extracted collagen, may be then suitably treated to separate the collagen material from the solution. In some embodiments of the present technology, after segregating the collagen-containing solution, the contacting the extracted collagen solution with a salt solution may include repeating until an at least about 95% to about 99.9% pure collagen precipitate is obtained. In some embodiments, the contacting may include salt solutions at concentrations of about 0.55 M to about 5 M. In certain embodiments, the salt solution concentrations may include, but not limited to, about 0.55 M to about 4 M, about 0.55 M to about 3 M, about 0.55 M to about 2 M, about 1 M to about 4 M, about 1 M to about 2.5 M, about 1 M to about 1.5 M, about 1.5 M to about 2.5 M, about, about 1 M to about 1.5 M, and ranges between any two of these values or less than any one of these values. Suitable salt solution concentrations may include about 0.55 M, about 0.75 M, about 1 M, about 1.5 M, about 2 M, about 2.5 M, about 3 M, about 3.5 M, about 4 M, about 4.5 M, about 5 M and ranges between any two of these values or less than any one of these values. In one embodiment, the contacting the extracted collagen solution with the salt solution may include salt solution concentrations of about 0.55 M to about 3 M. In another embodiment, the salt solution concentration may include concentrations of about 0.55 M to about 2 M. In yet another embodiment, the salt solution concentration may include concentrations of about 0.55 M to about 1.5 M. In particular embodiments, the salt solution concentrations may include concentrations less than about 1.5 M.

The salt solution may be added to the supernatant (i.e., extracted collagen solution) at a suitable rate to ensure maximum precipitation of the collagen material. In some embodiments, the method may include adding the salt solution at a rate of at least about 10 mL/min to about 20 mL/min. In certain embodiments, the rate includes, but not limited to, 10 mL/min to about 22 mL/min, about 10 mL/min to about 18 mL/min, about 10 mL/min to about 15 mL/min, about 12 mL/min to about 25 mL/min, about 15 mL/min to about 22 mL/min, and ranges between any two of these values or less than any one of these values. Suitable rates for adding the salt solution may include, but not limited to, at least about 10 mL/min, about 12 mL/min, about 15 mL/min, about 18 mL/min, about 20 mL/min, about 22 mL/min, about 25 mL/min and ranges between any two of these values or less than any one of these values. In certain embodiments, the salt solution may be added at ratio by weight of about 1:1 to about 2:1 salt solution to collagen-containing solution.

In certain embodiments, the salt solution treatment is followed by incubating the resulting solution over a period of 30 min to 1 week. In some embodiments, the incubating is from about 30 min to about 6 days, about 30 min to about 5 days, about 1 h to about 4 days, about 2 h to about 1 day, about 3 h to about 12 h, and ranges between any two of these values or less than any one of these values. Suitable incubation periods may include at least about 30 min, about 45 min, about 1 h, about 2 h, about 6 h, about 12 h, about 1 day, about 3 days, about 4 days, about 5 days, about 1 week and ranges between any two of these values or less than any one of these values.

In certain embodiments, the incubation is followed by centrifugation of the collagen precipitate mixture obtained. The centrifugation may include centrifuging the incubated solution at a force of about 5,000 G to about 25,000 G. Suitable centrifugation forces may include, but are not limited to, 5,000 G to about 20,000 G, about 5,000 G to about 15,000 G, about 5,000 G to about 12,000 G, and about 5,000 G to about 10,000 G. In certain embodiments, the centrifugation may include centrifuging over a period of about 5 min to about 60 min. Suitable centrifugation periods may include, but are not limited to, about 5 min to about 60 min, about 10 min to about 50 min, about 15 min to about 40 min, about 20 min to about 40 min, and ranges between any two of these values or less than any one of these values. Alternatively, suitable centrifugation periods may include, but are not limited to about 5 min, about 10 min, about 20 min, about 30 min, about 40 min, about 50 min, about 60 min and ranges between any two values or less than any one of these values. In one embodiment, the centrifugation may include centrifuging over a period of about 10 min to about 30 min. In some embodiments, the centrifugation may be conducted directly after the salt solution treatment without incubation.

The above described steps to obtain the collagen precipitate may be suitably repeated to obtain maximum recovery of the collagen precipitate. In certain embodiments, the method may include repeating the one or more of the contacting, salt treatment, incubation and separation procedures until an at least about 95% pure collagen precipitate is obtained. Suitable purities include, but are not limited to, about 95% to about 99.9%, about 96% to about 99.9%, about 97% to about 99.9%, about 98% to about 99.9%, about 99% to about 99.9%, about 99.5% to about 99.9%, and ranges in between any two values or less than any one of these values. In some embodiments, the collagen material is pure up to at least about 50% to about 99.9%, about 60% to about 99.9%, about 75% to about 99.9%, about 80% to about 99.9%, about 90% to about 99.9%, about 95% to about 99.9%, and ranges between any two of these values or less than any one of these values. In certain embodiments, the collagen precipitate purity is at least about 50%, about 60%, about 70%, about 75%, about 80%, about 85%, about 90%, about 95%, about 95.5%, about 96%, about 96.5%, about 97%, about 97.5%, about 98%, about 98.5%, about 99%, about 99.5%, about 99.9%, and ranges between any two of these values or less than any one of these values. In one embodiment, the one or more steps are repeated until an at least about 95% pure collagen precipitate is obtained. In another embodiment, the one or more steps are repeated until an at least about 99.9% pure collagen precipitate is obtained. The purity of the collagen precipitate may be determined by standard methods.

Any suitable salts can be used in the methods described above. Exemplary salts include, but are not limited to, sodium chloride, ammonium sulfate, and the like or combinations thereof. The salt solutions may include aqueous salt solutions.

The collagen precipitate is re-suspended in solution to obtain a re-suspended collagen solution. In some embodiments, the re-suspending may include contacting the collagen precipitate with a weak acid solution. Suitable weak acid solutions include, but are not limited to, solutions that maintain a pH buffer between about 2.8 to about 4. Suitable pH values include, but are not limited to, those disclosed above in any embodiment. In some embodiments, the weak acid solutions include solutions having a pKa between about 3 to about 7. Suitable pKa values for the weak acid solution include, but not limited to, those disclosed above in any embodiment. In some embodiments, the weak acid is in an amount, including but not limited to, about 0.01% to about 20.0% of the weak acid solution. Suitable weak acids include those disclosed above in any embodiment.

Based on the desired application, the re-suspended collagen solution may be subjected to further treatment to improve the purity or eliminate harmful agents. In some embodiments of the present technology, the method includes optionally performing a viral and prion inactivation step. The viral and prion inactivation may be conducted using various methods, including but not limited to, incubation in basic solution, gamma irradiation, UV irradiation, ethylene oxide treatment, $CO_2$ treatment, or combinations thereof. In some embodiments, the viral and prion inactivation includes incubation in basic solution. Suitable basic solutions include, but are not limited to, metal or ammonium hydroxides, acetates, citrates, formates, sulfates, and combinations thereof. In some embodiments, the metal includes, but is not limited to, alkali and alkaline earth metals. Suitable basic solutions of alkali and alkaline earth metals include, but are not limited to, sodium, potassium, calcium, and magnesium hydroxides, acetates, citrates, formates, sulfates, and combinations thereof.

In some embodiments, the incubation may include incubating the re-suspended collagen solution in a basic solution for a suitable period, including but not limited to, about 5 min, about 10 min, about 20 min, about 30 min, about 40 min, about 50 min, about 60 min, and ranges between any two of these values or less than any one of these values. Alternatively, suitable periods include about 5 min to about 1 h, about 10 min to about 1 h, about 30 min to about 1 h, about 45 min to about 1 h, and ranges between any two of these values or less than any one of these values. In one embodiment, the sodium hydroxide incubation period may include exposure times of about 15 min to about 45 min. In another embodiment, the period may include exposure times of about 30 min to about 1 h.

In some embodiments, the incubation may include base solution concentrations of up to about 4 M. Suitable concentrations include, but are not limited to, about 0.01 M to about 4 M, about 0.1 M to about 2 M, about 0.25 M to about 1.5 M, about 0.5 M to about 1 M, and ranges between any two of these values or less than any one of these values. In some embodiments, the viral and prion inactivation may further include adjusting the pH of the re-suspended collagen solution to a pH of about 2.8 to about 4 with a weak acid. In certain embodiments, the pH is adjusted to about 2.8 to about 3, about 3 to about 4, about 3.2 to about 4, about 3.5 to about 4, and ranges between any two of these values or less than any one of these values. In one embodiment, the method may include adjusting the pH of the re-suspended collagen solution with about 0.01% to about 20% weak acid solution to a pH of about 2.8 to about 4 after incubation.

As a result of the salt solution treatment, the re-suspended collagen solution may contain residual salt which may be removed using suitable desalting methods. Suitable desalting methods include, but are not limited to, buffer exchange filter concentration, dialysis, tangential flow filtration, ion exchange membrane process, and the like or combinations thereof. In one embodiment, desalting of the re-suspended collagen solution may include dialysis. The dialysis may include dialyzing the re-suspended collagen solution against an acid solution. Suitable acids used for dialyzing may include, but are not limited to, weak acids as disclosed herein in any embodiment. In certain embodiments, the dialyzing can include dialyzing the re-suspended collagen solution against an about 0.01% to about 20% weak acid solution. In certain embodiments, the dialysis is carried out over a period of up to about 2 weeks. The dialysis period may include, but is not limited to, about 12 h to about 2 weeks, about 18 h to about 12 days, about 1 day to about 1 week, and ranges between any two of these values or less than any one of these values. Suitable periods may include, but not limited to, about 2 h, about 6 h, about 12 h, about 18 h, about 1 day, about 3 days, about 5 days, about 7 days, about 9 days, about 12 days, about 14 days, and ranges between any two of these values or less than any one of these values. Suitable buffer solutions may be used during dialysis to maintain the pH of the solution. If used, the buffer may be exchanged with fresh buffer solution in between dialysis process. In one embodiment, the dialyzing is carried out against an about 0.01% to about 20% weak acid solution over a period of about 12 h to about 5 days, and may include exchanging the dialysis buffer after about 24 h.

In some embodiments, after desalting, the re-suspended collagen solution may be subjected to drying to obtain a collagen material. Suitable drying methods may include, but are not limited to, supercritical fluid drying, spray drying, cyclic pressure drying, inert medium drying, fluid bed drying, lyophilizing, dehydration, and the like or combinations thereof.

In some embodiments, the method further includes sterilizing the collagen material. Suitable methods for sterilization of the collagen material may include, but are not limited to, gamma irradiation, incubation with peracid, supercritical fluid treatment, and the like or combinations thereof. In some embodiments, the sterilizing includes gamma irradiation. In some embodiments, the method may include exposing collagen material to gamma radiation between about 0.01 Mrad to about 5 Mrad. Suitable gamma radiation amounts include about 0.01 Mrad to about 5 Mrad, about 0.1 Mrad to about 4.5 Mrad, about 0.5 Mrad to about 3.5 Mrad, about 1 Mrad to about 3 Mrad, and ranges between any two of these values or less than any one of these values. The gamma irradiation process may further include combining additional additives or minerals to the collagen material prior to irradiation.

In some embodiments, the sterilizing includes incubation with peracid. In some embodiments, the peracid incubation is performed via vapor incubation. In some embodiments, the peracid is present in an amount from about 0.01% to about 5%. Suitable amounts include, but are not limited to, about 0.01% to about 5%, about 0.01% to about 3%, about 0.01% to about 1%, about 0.05% to about 3%, about 0.05% to about 1%, about 0.05% to about 0.5%, about 0.1% to about 1%, about 0.5% to about 1%, about 0.5% to about 3%, and ranges between any two of these values or less than any one of these values. In some embodiments, the vapor incubation is performed at a flow rate of about 20 L/min to about 120 L/min. Suitable flow rates include, but are not limited to, about 20 L/min to about 100 L/min, about 40 L/min to about 90 L/min, or about 80 L/min to about 90 L/min. In some embodiments, the vapor incubation is carried for a duration from about 15 s to about 1 h. Suitable vapor incubation durations include, but are not limited to about 30 s to about 45 min, about 1 min to about 30 min, about 5 min to about 15 min, about 10 min to about 25 min, and ranges between any two of these values or less than any one of these values.

In some embodiments, the sterilizing includes supercritical fluid treatment (SCF). In some embodiments, the supercritical fluid includes, but is not limited to supercritical carbon dioxide, nitrous oxide, water, alcohol, acetone, and the like or combinations thereof. In some embodiments, the supercritical treatment is carried out at temperatures from about 27° C. to about 55° C. Suitable temperatures include about 27° C. to about 55° C., about 30° C. to about 45° C., about 35° C. to about 40° C., and ranges between any two of these values or less than any one of these values. In some embodiments, the supercritical fluid treatment is carried out at a pressure of about 75 bar to about 525 bar, about 100 bar to about 475 bar, about 250 bar to about 400 bar, about 300 bar to about 375 bar, and ranges between any two of these values or less than any one of these values. As demonstrated in FIG. 7, sterilized collagen material (e.g., peracid sterilized) exhibits no degradation in function when used in a bio gel composition, as compared to unsterilized collagen material.

The collagen material of the present technology may include dissolving the sterilized collagen material in a weak acid solution, as described herein. In some embodiments, the weak acid solution is an about 0.01% to about 3% weak acid solution. The sterilized collagen material may be dissolved in the weak acid solution in any concentration. Suitable concentrations include, but are not limited to, about 5 mg/mL to about 200 mg/mL, about 5 mg/mL to about 60 mg/mL, about 20 mg/mL to about 150 mg/mL, about 40 mg/mL to about 100 mg/mL, or about 60 mg/mL to about 90 mg/mL.

In some embodiments of the present technology, the method may include performing one or more steps of the method at a temperature of up to about 22° C. In some embodiments, the temperature may include, but not limited to, about 0° C. to about 22° C., about 0° C. to about 20° C., about 0° C. to about 12° C., about 0° C. to about 6° C., about 2° C. to about 6° C., and ranges between any two of these values or less than any one of these values.

In some embodiments of the present technology, the method may include performing one or more steps of the method in compliance with Good Manufacturing Practice (GMP) guidelines for aseptic preparation or aseptic processing, as promulgated by the U.S. Food and Drug Administration, for example. In one embodiment, the sterilized collagen material is in compliance with GMP guidelines. In at least one embodiment, the method of the present technology is a method according to the steps illustrated in FIG. 1.

In some embodiments, the methods of the present technology include processing a collagen-based biomaterial to obtain an about 100 μM to about 1 cm biomaterial particles, and optionally soaking the collagen-based biomaterial in alcohol and washing the biomaterial particles in a buffer solution; contacting the biomaterial particles with an about 0.01% to about 20% weak acid solution to obtain a collagen-containing solution; segregating the collagen-containing solution to obtain an extracted collagen solution; contacting the extracted collagen solution with a salt solution until an at least about 95% pure collagen precipitate is obtained; re-suspending the collagen precipitate in an about 0.01% to about 20% weak acid solution to obtain a re-suspended collagen solution; optionally, undergoing viral and prion inactivation of the re-suspended collagen solution; desalting the re-suspended collagen solution; drying the re-suspended collagen solution to obtain a collagen material; and sterilizing the collagen material by vapor incubation with peracid, and optionally suspending the sterilized collagen material in an about 0.01% to about 3% weak acid solution.

In another aspect of the present technology, a bio gel composition is provided, wherein the composition includes the collagen material obtained using the present method of harvesting collagen.

In another aspect of the present technology, a bio gel composition is provided, wherein the composition includes a collagen material as described above in any embodiment. The bio gel composition may include collagen material in a weak acid solution. The bio gel composition may be prepared using suitable amounts of collagen material. In some embodiments, the bio gel composition may include collagen material in an amount greater than 5 mg/mL. Suitable amounts of collagen material in the bio gel composition may include, but are not limited to, about 5 mg to about 200 mg/mL. The bio gel composition may undergo rapid gelation at room temperature. In some embodiments, the bio gel composition may undergo gelation in less than about 10 min, less than about 8 min, less than about 5 min, less than about 3 min, less than about 2 min, less than about 1 min, or less than about 30 s, and time periods in between any two of these values or less than any one of these values, at a temperature of about 25° C. to about 37° C. The bio gel composition of the present technology may also be liquid under a shear stress of 15 Pa to 100 Pa before gelation and remain solid under a hydrostatic pressure of about 30 Pa to about 120 Pa during gelation.

In some embodiments, the collagen material in the bio gel compositions may include collagen from a mammalian source. Suitable mammalian sources may include, but are not limited to, equine, canine, porcine, bovine, feline, caprine, ovine, murine, or human. In certain embodiments, the mammalian source is porcine, bovine, or a combination thereof. The collagen in the collagen material can be of any type and can be obtained from various sources including, but not limited to, tendon, skin, ligament, bone, teeth, cartilage, connective tissue, intervertebral disc, cornea, and the like and combinations thereof. In some embodiments, the collagen material selected from tendon, skin, bone, or combinations thereof. In certain embodiments, the collagen material may be derived from a mammalian source, including but not limited to, bovine, porcine, murine, or combinations thereof. When the source is tendon, it may include, but is not limited to, common digital extensor tendon, lateral extensor tendon, deep flexor tendon, or combinations thereof. In some embodiments of the present technology, the collagen material may include type I collagen. In some embodiments, the type I collagen may include insoluble collagen, collagen fibers, soluble collagen, and acid-soluble collagen. In certain embodiments, the type I collagen is soluble collagen, acid-soluble collage, or a combination thereof. In some embodiments, the type I collagen does not include atelocollagen.

In some embodiments of the present technology, the bio gel composition may include the collagen material in an amount of about 5 mg/mL to about 200 mg/mL in a weak acid solution. In certain embodiments, the amount of collagen material in the bio gel composition may include, but is not limited to, about 5 mg/mL to about 200 mg/mL, about 10 mg/mL to about 100 mg/mL, about 15 mg/mL to about 80 mg/mL, about 20 mg/mL to about 70 mg/mL, about 25 mg/mL to about 50 mg/mL, about 5 mg/mL to about 60 mg/mL, about 5 mg/mL to about 40 mg/mL, and ranges between any two of these values or less than any one of these values. In other embodiments, the amount of collagen material in the bio gel composition may include about 5 mg/mL, about 10 mg/mL, about 15 mg/mL, about 20 mg/mL, about 25 mg/mL, about 30 mg/mL, about 40 mg/mL, about 50 mg/mL, about 60 mg/mL, about 70 mg/mL, about 80 mg/mL, about 90 mg/mL, about 100 mg/mL, and ranges between any two values or less than any one of these values.

In some embodiments of the present technology, the collagen material is dissolved in a weak acid solution. The weak acid solution may include weak acid in amounts in the range of about 0.01% to about 20.0% of the weak acid solution. The amount of weak acid in the weak acid solution may include, but is not limited to, about 0.01% to about 20%, about 0.01% to about 10%, about 0.01% to about 3%, about 0.1% to about 3%, about 0.3% to about 8%, about 0.5% to about 5%, about 1% to about 3%, and ranges between any two of these values or less than any one of these values. Suitable weak acid solutions include the weak acid in an amount that is about 0.01%, about 0.05%, about 0.1%, about 0.25%, about 0.5%, about 1.0%, about 1.5%, about 2.0%, about 2.5%, about 3.0%, about 4.0%, about 5.0%, about 6.0%, about 7.0%, about 8.0%, about 9.0%, about 10.0%, about 12.5%, about 15.0%, about 20% of the weak acid solution and ranges between any two of these values or less than any one of these values. In some embodiments, the weak acid solution is an about 0.01% to about 3% weak acid solution. Suitable weak acid may include, but is not limited to, weak acid solutions as described herein in any embodiment.

The bio gel composition may suitably include carriers or non-natural additives. Suitable carriers include, but are not limited to, water, aqueous ionic salt solutions (e.g., sodium hydroxide), phosphate buffer saline (PBS), cell medium, fetal bovine serum (FBS), Dulbecco's minimum essential medium (DMEM), fibroblast growth factor (bFGF), and the like or combinations thereof. Suitable non-natural additives include, but are not limited to, cross-linking agents. Suitable cross-linking agents include, but are not limited to, riboflavin, ribose, polyethylene glycol (PEG), glutaraldehyde, 1-ethyl-3-(3-dimethylaminopropyl)-carbodiimide hydrochloride, genipin, chitosan, and the like or combinations thereof. In one embodiment, the bio gel composition includes ribose. In another embodiment, the bio gel composition includes riboflavin.

In some embodiments, the bio gel composition may include decorin in the amounts of about 0.01% to about 5% (w/v). Suitable amounts of decorin include, but not limited to, about 0.01% to about 3% (w/v), about 0.01% to about 2% (w/v), about 0.1% to about 5% (w/v), about 0.1% to about 3% (w/v), about 0.1% to about 2% (w/v), about 0.3% to about 5% (w/v), 0.3% to about 3% (w/v), about 0.3% to about 2% (w/v), and ranges between any two of these values or less than any one of these values. Decorin is a small cellular or pericellular matrix proteoglycan that is, on average, about 90 to about 140 kDa in molecular weight. The glycosaminoglycan chains of decorin contain chondroitin sulfate or dermatan sulfate.

In some embodiments, the bio gel composition may further include living cells. In some embodiments, the living cells include, but not limited to, epidermal cells, chondrocytes and other cells that form cartilage, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, or tracheal epithelial cells. In one embodiment, the bio gel composition includes chondrocytes cells. In some embodiments, the bio gel composition includes living cells and is maintained at physiological pH. In some embodiments, the bio gel composition has a pH of about 7.4.

In some embodiments of the present technology, the bio gel composition may further include maintaining the composition at a temperature of about 0° C. to about 12° C. before gelation. The temperatures may include, but are not limited to, about 0° C. to about 12° C., about 0° C. to about 10° C., about 2° C. to about 10° C., about 2° C. to about 6° C., about 3° C. to about 8° C., about 3° C. to about 6° C., and ranges between any two of these values or less than any one of these values. In certain embodiments, the maintaining may include, but is not limited to, temperatures of about 0° C., about 2° C., about 4° C., about 6° C., about 8° C., about 10° C., about 12° C. and ranges between any two of these values or less than any one of these values.

In some embodiments, the bio gel composition may be a liquid under shear stress greater than about 15 Pa. In certain embodiments, the bio gel composition becomes a liquid under shear stress in the amounts of about 15 Pa to about 100 Pa. Suitable shear stress amounts include, but are not limited to, about 15 Pa to about 100 Pa, about 20 Pa to about 100 Pa, about 25 Pa to about 90 Pa, about 30 Pa to about 90 Pa, and ranges between any two of these values or less than any one of these values. In some embodiments, the bio gel composition becomes liquid under shear stress of about 15 Pa, about 20 Pa, about 25 Pa, about 30 Pa, about 40 Pa, about 50 Pa, about 60 Pa, about 70 Pa, about 80 Pa, about 90 Pa, about 100 Pa.

The bio gel composition of the present technology, while at rest and under no shear stress, remains solid under its own weight during gelation. In some embodiments, the bio gel composition remains solid under a hydrostatic pressure of about 30 Pa to about 120 Pa. Suitable hydrostatic pressures include, but is not limited to, about 30 Pa to about 120 Pa, about 50 Pa to about 120 Pa, about 60 Pa to about 120 Pa, about 80 Pa to about 120 Pa, about 30 Pa to about 90 Pa, about 30 Pa to about 80 Pa, about 30 Pa to about 60 Pa, and ranges between any two of these values or less than any one of these values.

The bio gel composition may be suitably shaped or formed into a two- or three-dimensional structure. In some embodiments, the bio gel composition may hold the shape of a three-dimensional structure prior to gelation. In some embodiments, the three-dimensional structure may be shaped or formed using a modular fabrication system. Suitable modular fabrication systems may include, but are not limited to, injection molding, rotational molding, positive molds, negative molds, subtractive manufacturing, milling and machining, and 3D printing devices.

In one embodiment, the modular fabrication system is a 3D printing device. Suitable 3D printing devices may include, but are not limited to, 3D printing devices capable of non-aseptic or aseptic three-dimensional structure fabrication. In certain embodiments, the 3D printing device is an aseptic 3D printing device in compliance with GMP guidelines. In some embodiments, 3D structures may be fabricated using bio gels described herein in 3D printing systems as described in U.S. Patent Application Ser. No. 62/511,292 entitled "ASEPTIC PRINTER SYSTEM INCLUDING DUAL-ARM MECHANISM," filed on May 25, 2017 and having, the entire contents of which are hereby incorporated by reference for the background information and methods set forth therein.

In some embodiments of the present technology, the bio gel composition undergoes gelation in less than about 10 min at a temperature of about 25° C. to about 37° C. In certain embodiments, the bio gel composition may undergo gelation in less than about 30 s to about 10 min, less than about 1 min to about 5 min, less than about 30 s to about 3 min, less than about 30 s to about 2 min and any range between any two of these values or less than any one of these values. In one embodiment, the bio gel composition may undergo gelation in less than about 50 s, less than about 40 s, or less than about 30 s. In another embodiment, the gelation occurs in less than about 30 s, about 60 s, about 70 s, about 80 s, about 90 s, 100 s, about 110 s, about 120 s, about 130 s, about 140 s, about 150 s, about 180 s and ranges between any two values or less than any one of these values. In one embodiment, the bio gel composition undergoes gelation in less than 30 s.

In some embodiments of the present technology, the bio gel composition may include undergoing gelation at a temperature of about 25° C. to about 37° C. In certain embodiments, the gelation temperatures may include, but are not limited to, about 25° C. to about 37° C., about 27° C. to about 35° C., about 30° C. to about 33° C., and ranges between any two of these values or less than any one of these values. Suitable gelation temperatures may include, but are not limited to, about 25° C., about 27° C., about 30° C., about 32° C., about 35° C., about 37° C. and ranges between any two values or less than any one of these values. In one embodiment, the bio gel composition undergoes gelation at a temperature of about 30° C. to about 37° C. In one embodiment, the bio gel composition undergoes gelation in less than 30 s at a temperature of about 25° C. to about 37° C.

In some embodiments of the present technology, bio gel compositions may also undergo cross-linking induced by exposure to an initiator. Suitable cross-linking initiators include, but are not limited to, ultraviolet (UV) irradiation, gamma radiation, and dehydrothermal treatment (DHT). In some embodiments, the cross-linking initiator is UV irradiation. In some embodiments, the initiator induces cross-linking of the bio gel composition as described herein in the absence of cross-linking agents. In some embodiments, the initiator induces cross-linking of a cross-linking agent in the bio gel composition. In some embodiments, the cross-linking agent includes, but is not limited to, cross-linking agents as described herein. In some embodiments, the cross-linking agent is riboflavin, ribose, and the like or combinations thereof.

In some embodiments, the bio gel composition may be formed into a three-dimensional structure which remains solid, and/or maintains its shape, under gravity after gelation. The structures formed by the bio gel compositions of the present technology exhibit reduced sagging and increased elasticity compared to other standard bio gel materials. In certain embodiments, the three-dimensional structure which includes the bio gel sags less than about 1% to about 30% of its height under gravity. The three-dimensional structure may sag less than about 1% to about 30%, about 2% to about 25%, about 3% to about 20%, about 4% to about 15%, about 5% to about 10% of its height under gravity, and ranges between any two of these values or less than any one of these values. In certain embodiments, the three-dimensional structure sags less than about 30%, about 25%, about 20%, about 15%, about 10%, about 5%, about 4%, about 3%, about 2%, about 1% of its height under gravity and ranges between any two of these values or less than any one of these values.

In some embodiments, the bio gel composition in a three-dimensional structure sags less than about 1% to about 30% of its height over a period of time, such as about 60 s to about 120 s. Periods include, but are not limited to, about 5 s to about 120 s, about 20 s to about 100 s, about 30 s to about 80 s, about 45 s to about 60 s, about 60 s to about 120 s, and ranges between any two of these values or less than any one of these values. The structures sags less than about 1% to about 30% reduction in its original height over suitable periods of time, which may include, but is not limited to, about 5 s, about 10 s, about 20 s, about 30 s, about 40 s, about 50 s, about 60 s, about 120 s and ranges between any two of these values or less than any one of these values. In one embodiment, the bio gel composition in the three-dimensional structure sags less than about 30% of its height under gravity over a 60 s period.

The bio gel compositions of the present technology may possess improved storage modulus. In some embodiments of the present technology, the bio gel composition may increase its storage modulus to up to about 5000% after gelation. The storage modulus may increase up to about 10% to about 5000%, about 50% to about 5000%, about 100% to about 5000%, about 500% to about 5000%, about 1000% to about 5000%, about 2500% to about 5000%, and ranges in between any two of these values or less than any one of these values. In certain embodiments, the bio gel composition may include, but is not limited to, increasing its storage modulus after gelation by up to about 100%, about 500%, about 1000%, about 2000%, about 3000%, about 4000%, about 5000%, and ranges between any two of these values or less than any one of these values. In one embodiment, the bio gel composition may include increasing its storage modulus by 5000%. In some embodiments, the bio gel composition may include increasing its storage modulus in about 1 min to about 5 min. Suitable periods include about 1 min to about 5 min, about 1 min to about 3 min, about 1 min to about 2 min, and ranges between any two of these values or less than any one of these values.

The bio gel compositions of the present technology may possess improved compressive strength. In some embodiments, the bio gel composition exhibits a stress/strain ratio greater than 1 kPa after gelation. The stress/strain ratio may be from about 1 kPa to about 100 kPa, about 1 kPa to about 60 kPa, about 5 kPa to about 50 kPa, about 5 kPa to about 40 kPa, and ranges in between any two of these values or less than any one of these values. In certain embodiments, the bio gel composition may exhibit a stress/strain ratio after gelation of about 1 kPa, about 5 kPa, about 7 kPa, about 8 kPa, about 9 kPa, about 10 kPa, about 11 kPa, about 12 kPa, about 14 kPa, about 16 kPa, about 18 kPa, about 20 kPa, about 25 kPa, about 30 kPa, about 35 kPa, about 40 kPa, about 50 kPa, about 60 kPa, about 70 kPa, about 80 kPa, about 90 kPa, about 100 kPa, and ranges between any two of these values or less than any one of these values.

In some embodiments, the bio gel composition may include a type I collagen material harvested as described herein in any embodiment. The type I collagen material may include amounts from about 5 mg/mL or greater. The bio gel composition may include the collagen material in an about 0.01% to about 3% weak acid solution. The bio gel composition of the present technology may include undergoing gelation in less than about 30 s at a temperatures from about 25° C. to about 37° C. The bio gel composition may further include about 0.01% to about 5% (w/v) decorin. Optionally, the bio gel composition may further include living cells. The bio gel composition may include becoming liquid under a shear stress of about 15 Pa to about 100 Pa. In some embodiments, the bio gel composition remains solid under a hydrostatic pressure of about 30 Pa to about 120 Pa during gelation. The bio gel composition may be shaped in a three-dimensional structure with a 3D printer. The bio gel composition may include holding a solid three-dimensional structure shape under gravity after the bio gel composition undergoes gelation. In some embodiments, the three-dimensional structure sags less than about 30% of its height under gravity over a period of about 60 s. The bio gel composition may include increasing its storage modulus up to about 5000% after gelation.

In one embodiment, the bio gel composition includes about 5 mg/mL to about 200 mg/mL of a collagen material, harvested using the methods as described herein in any embodiment, in an about 0.01% to about 3% weak acid solution; 0.1% to about 5% (w/v) decorin and, optionally, living cells; wherein the bio gel may undergo gelation in less than about 30 s at a temperatures from about 25° C. to about 37° C.; and wherein before gelation, the bio gel composition is a liquid under a shear stress of about 15 Pa to about 100 Pa, remains solid under a hydrostatic pressure of about 30 Pa to about 120 Pa during gelation; and further wherein after gelation, the bio gel composition may has an up to about 5000% increase in storage modulus, and maintains a three-dimensional shape, wherein the bio gel composition sags less than about 1% to about 30% of its height under gravity over about 60 s.

In another embodiment, the bio gel composition includes about 5 mg/mL to about 60 mg/mL of a type I collagen material, harvested from bovine, porcine, and/or murine sources as described herein, in an about 0.01% to about 3% weak acid solution; 0.1% to about 5% (w/v) decorin, carriers, cross-linking agents selected from riboflavin, ribose, or a combination thereof, and, optionally, living cells at pH 7.4; wherein the bio gel may undergo gelation in less than about 30 s at a temperature of about 35° C.; and wherein before gelation, the bio gel composition is a liquid under a shear stress of about 15 Pa to about 100 Pa, remains solid under a hydrostatic pressure of about 30 Pa to about 120 Pa during gelation; and further wherein after gelation, the bio gel composition may has an up to about 5000% increase in storage modulus, and maintains a three-dimensional shape, wherein the bio gel composition sags less than about 1% to about 30% of its height under gravity over about 60 s; and the bio gel composition exhibits a stress/strain ratio greater than 1 kPa after gelation.

In yet another aspect of the present technology, provided is a method of preparing a three-dimensional structure from the bio gel composition of the present technology, wherein the method includes providing a bio gel composition to a modular fabrication system, maintaining the bio gel composition at a temperature of about 0° C. to about 12° C., depositing the bio gel composition to form a three-dimensional structure, wherein the three-dimensional structure undergoes gelation; and curing the three-dimensional structure. The bio gel composition used in the method of preparing a three-dimensional structure may include a collagen material of the present technology in an amount greater than 5 mg/mL in a weak acid solution.

In some embodiments of the present technology, the method includes providing a bio gel composition, as described above in any embodiment, to a modular fabrication system. Suitable modular fabrication systems may include, but are not limited to, systems described herein in any embodiment, In some embodiments, the modular fabrication system may include a 3D printing device. In some embodiments, the 3D printing device may be a non-aseptic or aseptic device. In one embodiment, the 3D printing device is an aseptic 3D printing device as described in this application herein.

The method includes providing a bio gel composition as described in this application herein. In some embodiments of the present technology, the method includes providing a bio gel composition that includes a collagen material in amounts of 5 mg/mL or greater in a weak acid solution. In some embodiments, the collagen material may be derived from a mammalian source, including but not limited to, bovine, porcine, and/or murine sources. In some embodiments, the collagen material may include type I collagen. In some embodiments of the present technology, the collagen material is in a weak acid solution, such as an about 0.01% to about 3% weak acid solution. In some embodiments of the present technology, the method includes providing a bio gel composition that may further include cross-linking agents, such as about 0.01% to about 5% (w/v) decorin. In some embodiments, the bio gel composition includes carriers and non-natural additives as described herein in any embodiment. In some embodiments, the bio gel composition may include living cells. In some embodiments of the present technology, the method includes providing the bio gel composition that may be liquid under a shear stress of about 15 Pa to about 100 Pa. In some embodiments, the bio gel composition remains solid under a hydrostatic pressure of about 30 Pa to about 120 Pa during gelation.

The method includes maintaining the bio gel composition at a suitable temperature after providing it to a modular fabrication system. In some embodiments of the present technology, the method includes maintaining the bio gel composition at a temperature of about 0° C. to about 12° C. before gelation. The temperatures may include, but are not limited to, about 0° C. to about 12° C., about 0° C. to about 10° C., about 2° C. to about 10° C., about 2° C. to about 6° C., about 3° C. to about 8° C., about 3° C. to about 6° C., and ranges between any two of these values or less than any one of these values. In certain embodiments, the maintaining may include, but is not limited to, temperatures of about 0° C., about 2° C., about 4° C., about 6° C., about 8° C., about 10° C., about 12° C. and ranges between any two of these values or less than any one of these values.

The bio gel composition is deposited into a two- or three-dimensional structure at a suitable maintenance temperature. In some embodiments, the depositing may include depositing the bio gel composition at an extrusion rate of about 30 mm$^3$/s to about 80 mm$^3$/s. Suitable extrusion rates include, but not limited to, about 30 mm$^3$/s to about 80 mm$^3$/s, about 40 mm$^3$/s to about 80 mm$^3$/s, about 50 mm$^3$/s to about 80 mm$^3$/s, about 60 mm$^3$/s to about 80 mm$^3$/s, and ranges between any two of these values or less than any one of these values.

As part of the bio gel deposition step, the three-dimensional structure may also undergo gelation. In some embodiments, the depositing of the bio gel composition into a three-dimensional structure further includes undergoing gelation in less than about 10 min at a temperature of about 25° C. to about 37° C. In certain embodiments, the three-dimensional structure may undergo gelation in less than about 30 s to about 10 min, less than about 1 min to about 5 min, less than about 30 s to about 3 min, less than about 30 s to about 2 min and any range between any two of these values or less than any one of these values. In one embodiment, the bio gel composition may undergo gelation in less than about 50 s, less than about 40 s, or less than about 30 s. In another embodiment, the gelation occurs in less than about 30 s, about 60 s, about 70 s, about 80 s, about 90 s, 100 s, about 110 s, about 120 s, about 130 s, about 140 s, about 150 s, about 180 s and ranges between any two values or less than any one of these values. In one embodiment, the bio gel composition undergoes gelation in less than 30 s.

In some embodiments of the present technology, the three-dimensional structure may include undergoing gelation at a temperature of about 25° C. to about 37° C. In certain embodiments, the gelation temperatures may include, but not limited to, about 25° C. to about 37° C., about 27° C. to about 35° C., about 30° C. to about 33° C., and ranges between any two of these values or less than any one of these values. Suitable gelation temperatures may include, but not limited to, about 25° C., about 27° C., about 30° C., about 32° C., about 35° C., about 37° C. and ranges between any two values or less than any one of these values. In one embodiment, the three-dimensional structure may undergo gelation at temperatures of about 30° C. to about 37° C. In one embodiment, the bio gel composition undergoes gelation in less than 30 s at a temperature of about 25° C. to about 37° C.

In some embodiments of the present technology, the depositing may include gelation of the three-dimensional structure sequentially, simultaneously, or separately to form the three-dimensional structure. In certain embodiments, the depositing the bio gel composition may include sequential gelation of the bio gel composition immediately after the three-dimensional structure is formed. In another embodiment, the depositing may include simultaneous gelation (i.e., concurrently or overlapping) of the bio gel composition as the three-dimensional structure is formed. In yet another embodiment, the depositing may include gelation separately from depositing the bio gel composition to form the three-dimensional structure, which may include gelation after a period of about 5 min to about 24 h after forming the three-dimensional structure.

In some embodiments, the bio gel composition may form a three-dimensional structure which remains solid, and/or maintains its shape, under gravity after gelation. The structures formed by the bio gel compositions of the present technology exhibit reduced sagging and increased elasticity compared to other bio gel materials known in the art. In certain embodiments, the three-dimensional structure which includes the bio gel sags less than about 1% to about 30% of its height under gravity. The three-dimensional structure may sag less than about 1% to about 30%, about 2% to about 25%, about 3% to about 20%, about 4% to about 15%, about 5% to about 10% of its height under gravity, and ranges between any two of these values or less than any one of these values. In certain embodiments, the three-dimensional structure sags less than about 30%, about 25%, about 20%, about 15%, about 10%, about 5%, about 4%, about 3%, about 2%, about 1% of its height under gravity and ranges between any two of these values or less than any one of these values.

In some embodiments, the three-dimensional structure sags less than about 1% to about 30% of its height over a period of time, such as about 60 s to about 120 s. Periods include, but not limited to, about 5 s to about 120 s, about 20 s to about 100 s, about 30 s to about 80 s, about 45 s to about 60 s, about 60 s to about 120 s, and ranges between any two of these values or less than any one of these values. The structures sag less than 1% to about 30% reduction in its original height over suitable periods of time, which may include, but are not limited to, about 5 s, about 10 s, about 20 s, about 30 s, about 40 s, about 50 s, about 60 s, about 120 s and ranges between any two of these values or less than any one of these values. In one embodiment, the three-dimensional structure sags less than about 30% of its height under gravity over a 60 s period.

In some embodiments of the present technology, the storage modulus of the three-dimensional structure may increase to up to about 5000% after gelation. The storage modulus may increase up to about 10% to about 5000%, about 50% to about 5000%, about 100% to about 5000%, about 500% to about 5000%, about 1000% to about 5000%, about 2500% to about 5000%, and ranges in between any two of these values or less than any one of these values. In certain embodiments, the bio gel composition may include, but is not limited to, increasing its storage modulus after gelation by up to about 100%, about 500%, about 1000%, about 2000%, about 3000%, about 4000%, about 5000%, and ranges between any two of these values or less than any one of these values. In one embodiment, the bio gel composition may include increasing its storage modulus by 5000%. In some embodiments, the bio gel composition may include increasing its storage modulus in about 1 min to about 5 min. Suitable periods include about 1 min to about 5 min, about 1 min to about 3 min, about 1 min to about 2 min, and ranges between any two of these values or less than any one of these values. In some embodiments, the three-dimensional structure exhibits a stress/strain ratio greater than 1 kPa after gelation. The stress/strain ratio may be from about 1 kPa to about 100 kPa, about 1 kPa to about 60 kPa, about 5 kPa to about 50 kPa, about 5 kPa to about 40 kPa, and ranges in between any two of these values or less than any one of these values.

The three-dimensional structure, deposited from the bio gel composition, undergoes a curing step following gelation. In some embodiments, the method includes curing the three-dimensional structure at a temperature of about 34° C. to about 37° C. Suitable curing temperatures may include, but not limited to, about 34° C. to about 37° C., about 35° C. to about 37° C., about 36° C. to about 37° C., and ranges between any two of these values or less than any one of these values. The three-dimensional structure may also be placed in a buffer solution during the curing step. In some embodiments, suitable buffer solutions include, but not limited to, phosphate buffered saline, sodium chloride solution, phosphates, and phosphate buffer solution. In some embodiments, the method may further include curing the three-dimensional structure in buffer solution and cell medium. Suitable cell medium may include, but is not limited to, serum, serum-free medium, HEPES, DMEM, bFGF, FBS, and the like or combinations thereof.

In some embodiments, the methods of the present technology may further include curing the three-dimensional structures formed from bio gel compositions by exposure to cross-linking initiators as described herein. In some embodiments, the curing also includes exposing the three-dimensional structure to UV irradiation. The duration of UV irradiation is not specifically limited and is determined based on various factors, including but not limited to, size, shape, height, thickness, and the like of the three-dimensional structure and the distance of the UV light source. In some embodiments, the three-dimensional structure formed from the bio gel includes cross-linking agents as described herein in any embodiment. In certain embodiments, the cross-linking agents include ribose, riboflavin, or a combination thereof.

Figure 2:
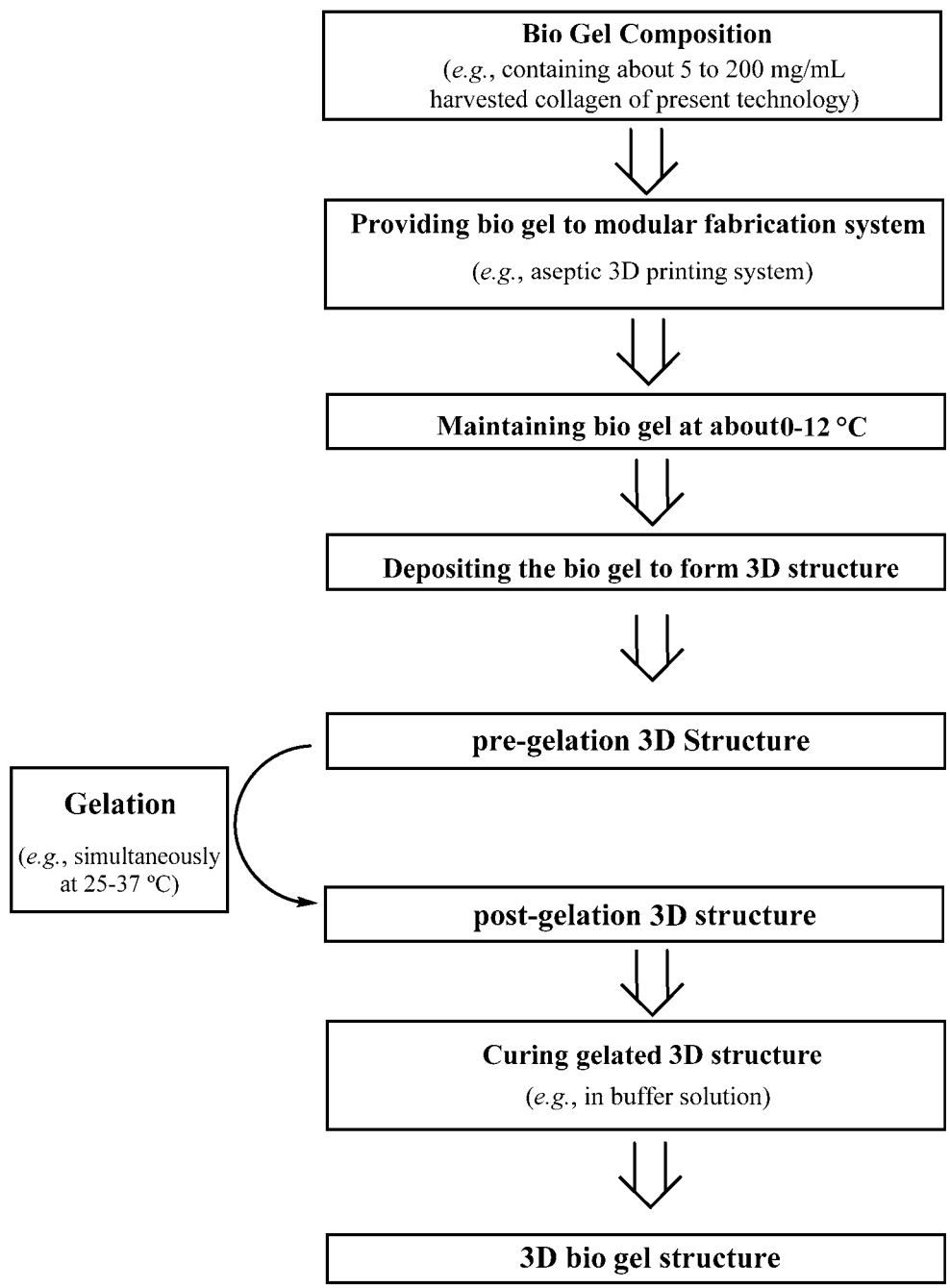
FIG. 2 is a flow chart depicting an exemplary method of preparing a three-dimensional structure from the bio gel composition of the present technology.

In some embodiments of the present technology, the method includes providing a bio gel composition, which includes type I collagen material derived from bovine, porcine, murine sources, to an 3D printing device. The bio gel composition includes collagen material in a 0.01% to about 3% weak acid solution and includes about 0.01% to about 5% (w/v) decorin. The bio gel composition may further include cross-linking agents or living cells, and has a pH of about 7.4. The bio gel composition is liquid under shear stress of about 15 Pa to about 100 Pa, and remains solid under a hydrostatic pressure of about 30 Pa to about 120 Pa during gelation. The method includes maintaining the bio gel composition at a temperature of about 0° C. to about 12° C. While maintaining the bio gel composition at about 0° C. to about 12° C., the method includes depositing the bio gel composition to form a three-dimensional structure. The method includes depositing the bio gel composition to form the three-dimensional structure simultaneously with gelation at a temperature of about 25° C. to about 37° C. over a period of less than about 30 s. The three-dimensional structure may include remaining solid under gravity such that the three-dimensional structure sags less than about 1% to about 30% of its height over a period of about 60 s after gelation. The three-dimensional structure, after gelation, may include an increase in storage modulus of up to about 5000%. In some embodiments, the three-dimensional structure exhibits a stress/strain ratio greater than 1 kPa after gelation. The method includes curing the three-dimensional structure at a temperature of about 34° C. to about 37° C. in a buffer solution. In at least one embodiment, the method of the present technology is a method according to the steps illustrated in FIG. 2.

In one embodiment of the present technology, the method includes providing to an aseptic 3D printer, a bio gel composition as described herein, which includes a type I collagen material derived from bovine, porcine, and/or murine sources, in an about 0.01% to about 3% weak acid solution, and may further include 0.1% to about 5% (w/v) decorin, and optionally cross-linking agents and living cells; maintaining the bio gel composition at a temperature of about 0° C. to about 12° C.; depositing the bio gel composition at an extrusion rate of about 30 mm$^3$/s to about 80 mm$^3$/s to form a three-dimensional structure, where the three-dimensional structure also undergoes gelation in less than about 30 s at about 25° C. to about 37° C.; and curing the three-dimensional structure at about 34° C. to about 37° C. in a phosphate buffer solution.

In another aspect, a method of preparing a bio gel composition for use in three-dimensional structure fabrication, wherein the method includes providing a first receptacle having a collagen material in a weak acid solution; providing a second receptacle having a carrier; and contacting the collagen material in weak acid solution of the first receptacle with the carrier of the second receptacle to obtain a bio gel composition having a homogeneity of about 50% to about 99.9%.

The method provides a first receptacle having a collagen material harvested by methods described in this application herein. In some embodiments of the present technology, the method includes the collagen material in amounts of 5 mg/mL or greater in a weak acid solution. In one embodiment, the first receptacle may include the collagen material in amounts of about 5 mg/mL to about 200 mg/mL. In some embodiments, the collagen material may be derived from tendon from a natural source, including but not limited to, bovine or porcine sources. In some embodiments, the collagen material may include type I collagen. In some embodiments of the present technology, the collagen material may further include about 0.01% to about 5% (w/v) decorin.

In some embodiments of the present technology, the weak acid in the weak acid solution may be present in amounts of about 0.01% to about 20.0% of the weak acid solution. The amount of weak acid in the weak acid solution may include, but is not limited to, about 0.01% to about 20%, about 0.01% to about 10%, about 0.01% to about 3%, about 0.1% to about 3%, about 0.3% to about 8%, about 0.5% to about 5%, about 1% to about 3%, and ranges between any two of these values or less than any one of these values. Suitable weak acid solutions include the weak acid in an amount that is about 0.01%, about 0.05%, about 0.1%, about 0.25%, about 0.5%, about 1.0%, about 1.5%, about 2.0%, about 2.5%, about 3.0%, about 4.0%, about 5.0%, about 6.0%, about 7.0%, about 8.0%, about 9.0%, about 10.0%, about 12.5%, about 15.0%, about 20% of the weak acid solution and ranges between any two of these values or less than any one of these values. In some embodiments, the weak acid solution is an about 0.01% to about 3% weak acid solution. In some embodiments, the weak acid solution may include, but not limited to, weak acid solutions having a pH of about 2.8 to about 4. Suitable weak acid may include, but is not limited to, weak acid solutions as described herein in any embodiment.

The method further provides a second receptacle having carriers, and optionally cross-linking agents as described herein in any embodiment. Suitable carriers include, but are not limited to, water, aqueous sodium hydroxide, PBS, DMEM, and the like or combinations thereof. Suitable cross-linking agents include, but are not limited to, riboflavin, ribose, and the like or combinations thereof.

The method may optionally include providing a third receptacle of living cells. Suitable living cells may include, but not limited to, epidermal cells, chondrocytes and other cells that form cartilage, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, or tracheal epithelial cells. In one embodiment, the third receptacle includes chondrocyte cells. In some embodiments, the living cells are maintained at a physiological pH in a cell medium. In some embodiments, the living cells in the third receptacle are maintained at a pH of about 7.4. Suitable cell medium may include those described herein.

The collagen material in the first receptacle and weak acid solution in the second receptacle are contacted to obtain a bio gel composition having sufficient homogeneity. In some embodiments of the present technology, the contacting may include, but is not limited to, mixing, stirring, agitating, oscillating, and the like or combinations thereof. In certain embodiments, the contacting includes oscillating, such as manual or automated oscillation. In one embodiment, the contacting includes manual oscillation. In another embodiment, the contacting includes mixing, such as a manual or The materials in the first, second, and optionally third receptacle may be released sequentially or simultaneous in a suitable order. In some embodiments, the contacting produces a bio gel composition having about 50% to about 99.9% homogeneity. Suitable homogeneities include, but are not limited to, about 50% to about 99.9%, about 60% to about 99.9%, about 70% to about 99.9%, about 80% to about 99.9%, about 90% to about 99.9% about 95% to about 99.9%, and ranges between any two of these values and less than any one of these values. In certain embodiments, the homogeneity is about 50%, about 55%, about 60% about, about 65%, about 70%, about 75%, about 80%, about 85%, about 90%, about 95%, about 97%, about 99.9%, and ranges between any two of these values or less than any one of these values. In some embodiments of the present technology, the method further includes, optionally, contacting the third receptacle of livings cells with the collagen material and weak acid solutions to obtain a bio gel composition having about 50% to about 99.9% homogeneity. Homogeneity is assessed using standard methods.

The bio gel composition obtained after contacting the collagen material with the weak acid solution may be, optionally, maintained at a suitable temperature. In some embodiments, the maintaining the bio gel composition may be at temperatures of about 0° C. to about 12° C. before gelation. The temperatures may include, but are not limited to, about 0° C. to about 12° C., about 0° C. to about 10° C., about 2° C. to about 10° C., about 2° C. to about 6° C., about 3° C. to about 8° C., about 3° C. to about 6° C., and ranges between any two of these values or less than any one of these values. In certain embodiments, the maintaining may include, but is not limited to, temperatures of about 0° C., about 2° C., about 4° C., about 6° C., about 8° C., about 10°

C., about 12° C. and ranges between any two of these values or less than any one of these values.

A three-dimensional structure may be fabricated from the bio gel composition. In some embodiments, the method further includes fabricating a three-dimensional structure using the bio gel composition. In some embodiments, the fabricating may be sequential to, simultaneous with, or separate from the contacting the collagen material with the weak acid solution to form the bio gel composition. In one embodiment, the method may include fabricating the three-dimensional structure sequentially with, i.e., immediately after, the contacting step. In another embodiment, the method may include fabricating the three-dimensional structure simultaneously with, i.e., concurrently or overlapping, the contacting step. In yet another embodiment, the method may include fabricating the three-dimensional structure separately from the contacting step, such as storing the resultant bio gel composition at a temperature of about 0° C. to about 12° C. over a period of about 6 h to about 2 weeks. In certain embodiments, the bio gel composition may include storing at about 2° C. to about 6° C. for a period of about 6 h to about 2 weeks, about 12 h to about 1 week, about 24 h to about 6 days, about 48 h to about 5 days, and ranges between any two of these values or less than any one of these values.

In some embodiments, the method includes fabricating the three-dimensional structure by providing the bio gel composition to a modular fabrication system as described herein. In some embodiments, the modular fabrication system may include a 3D printing device. In one embodiment, the 3D printing device is aseptically clean and is in compliance with GMP guidelines.

In some embodiments, the method may include fabricating the three-dimensional structure by depositing the bio gel composition at 30 mm$^3$/s to about 80 mm$^3$/s. Suitable extrusion rates include, but not limited to, about 30 mm$^3$/s to about 80 mm$^3$/s, about 40 mm$^3$/s to about 80 mm$^3$/s, about 50 mm$^3$/s to about 80 mm$^3$/s, about 60 mm$^3$/s to about 80 mm$^3$/s, and ranges between any two of these values or less than any one of these values. In some embodiments, the depositing may further include gelation of the three-dimensional structure in less than about 3 min at a temperature of about 25° C. to about 37° C. as described herein. In some embodiments of the present technology, the fabricating may include depositing the bio gel composition where gelation occurs sequentially, simultaneously, or separately to forming the three-dimensional structure.

In some embodiments of the present technology, the method includes fabricating a three-dimensional structure that remains solid, or maintains its shape, under gravity after gelation as described herein. In certain embodiments, the three-dimensional structure sags less than about 1% to about 30% of its height under gravity over a period of up to about 60 s to about 120 s. In one embodiment, the three-dimensional structure sags less than about 30% of its height under gravity over an about 60 s period. As described herein, the three-dimensional structure may be very strong and improve storage modulus. In certain embodiments, the three-dimensional structure may increase its storage modulus by up to about 5000% after gelation. In some embodiments, the three-dimensional structure exhibits a stress/strain ratio greater than 1 kPa after gelation. In certain embodiments, the stress/strain ratio is about 1 kPa to about 60 kPa. Further and as described herein, the method may further include curing the three-dimensional structure. In certain embodiments, the curing may be at temperatures from about 34° C. to about 37° C. in phosphate buffer solution. In some embodiments, the curing the three-dimensional structure may be in buffer solution and cell medium as described herein.

In some embodiments, the methods and compositions disclosed herein in any embodiment are in compliance with GMP guidelines. In at least one embodiment, the method of the present technology is a method according to the steps illustrated in FIG. 3.

In one embodiment of the present technology, the method includes providing a type I collagen material derived from bovine, porcine, and/or murine sources in an about 0.01% to about 3% weak acid solution in a first receptacle in an amount greater than about 5 mg/mL; providing a carrier solution, and optionally a cross-linking agent, in a second receptacle, where the carrier includes PBS, water, and aqueous sodium hydroxide and the cross-linking agent includes riboflavin, ribose, or a combination thereof; optionally, providing a third receptacle having living cells in cell medium, where the cell medium is DMEM; contacting the type I collagen material in about 0.01% to about 3% weak acid of the first receptacle with the carriers in the second receptacle, and optionally with the living cells in cell medium of the third receptacle, to obtain a bio gel composition having a homogeneity of greater than about 99%; and optionally, fabricating the bio gel composition into a three-dimensional structure using an aseptic 3D printing device.

The present technology, thus generally described, will be understood more readily by reference to the following examples, which are provided by way of illustration and are not intended to be limiting of the present technology.

EXAMPLES

Example 1: Process of Harvesting Collagen

This example provides a process for harvesting collagen from mammalian sources, for example, skin, tendon, or bone from porcine, bovine, or murine derived collagen sources, as illustrated in FIG. 1. Extracellular matrix and infiltrates were removed from the collagen-based biomaterial. The resulting collagen-based biomaterial was soaked in alcohol. The collagen-based biomaterial was then mechanically processed until greater than 95% of the material was reduced to less than 1 mm biomaterial particles.

The biomaterial particles were washed by adding to a buffer solution and stirring, following which the biomaterial particles were allowed to settle and the buffer solution was poured off. The biomaterial particles were then added to distilled $H_2O$ (di$H_2O$) and stirred. The biomaterial particles were then allowed to settle and the di$H_2O$ was poured off. The biomaterial particles were added to a 0.01% to 20% weak acid solution and stirred. The mixture was centrifuged, and the supernatant was collected while the pellets were discarded.

The supernatant was combined with a 0.55 M to 5 M salt solution and stirred. The supernatant/salt solution was centrifuged, and the resultant pellets were collected while the supernatant was discarded. The pelleted material was re-suspended in a 0.1% to 20% weak acid solution.

The re-suspended material was combined with a metal hydroxide solution, and stirred. Immediately after, the mixture was readjusted to acidic conditions (pH of 3-4). The mixture was then dialyzed against 0.01% to 20% weak acid solution following which it was removed from the dialysis tubing and dried. The resulting collagen material was sterilized via vapor incubation with peracid, gamma irradiation, ethylene oxide, or critical $CO_2$ treatment. The sterilized collagen material was suspended in a 0.01% to 3% weak acid solution to an appropriate concentration for storage for up to 3 to 7 days. Weak acid, buffer solutions, and salt solutions include those described herein.

Example 2: Preparation of Bio Gel Compositions

Figure 3:
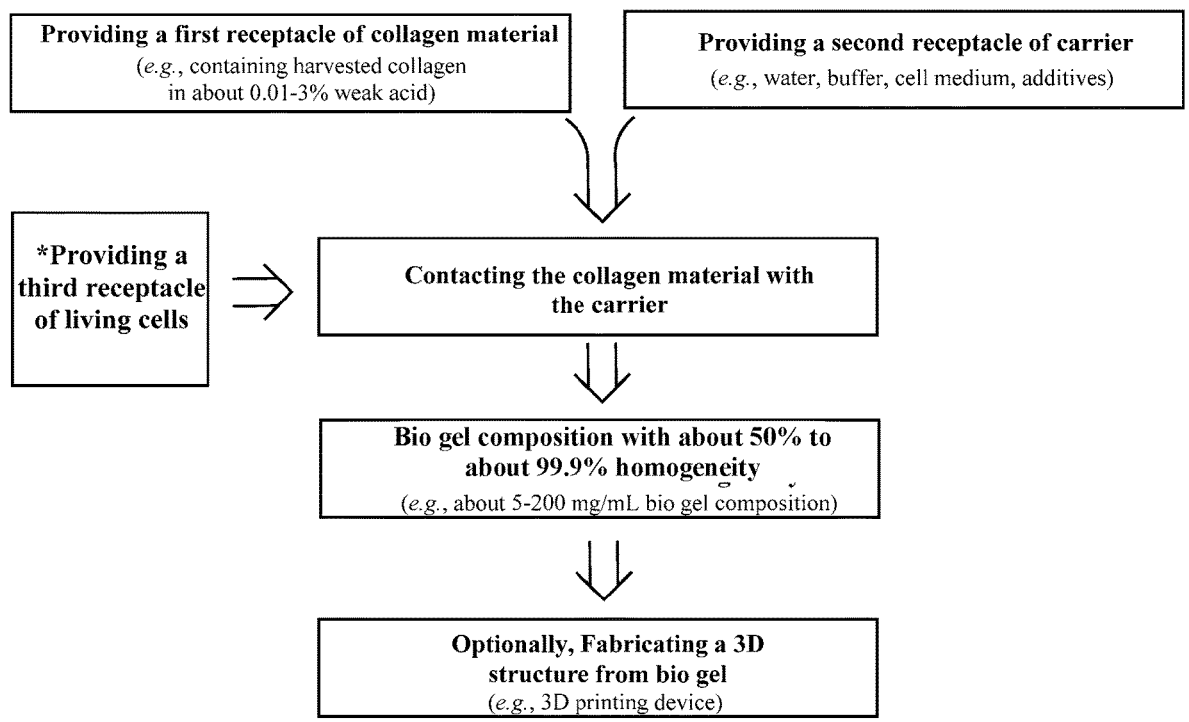
FIG. 3 is a flow chart depicting an exemplary method of preparing the bio gel composition of the present technology to fabricate a three-dimensional structure.

Bio gel compositions, which are suitable for use as printable inks for molds and 3D printing devices as described herein, were prepared as illustrated in FIG. 3 and using harvested sterilized collagen according to Example 1. Acellular bio gel Compositions A-J were prepared as follows: A stock solution of harvested sterilized collagen (Example 1) in 0.01-3% weak acid mixed with a carrier solution. The mixture was adjusted to physiological pH. The resulting mixture produced bio gel compositions containing 5-60 mg/mL of harvested sterilized collagen from Example 1. Bio gel compositions H, I, and J illustrate curable bio gel compositions, which include cross-linking agents.

Comparative bio gel compositions were prepared according to the procedure described for compositions A-J. Commercially available purified pharmaceutical-grade collagens X (bovine dermis derived Collagen Type I), Y (porcine tissue derived Collagen Type I), and Z (bovine dermis derived Collagen Type I) were not obtained by the methods described herein, and do not have the properties described herein for the present technology.

Cellular bio gel Compositions K-R were prepared as follows: A stock solution of harvested sterilized collagen (Example 1) in 0.01-3% weak acid solution was added through a stopcock apparatus to a carrier solution. Living cells in cell media were added to the mixture and adjusted to neutral pH. The resulting mixture produced cellular bio gel compositions containing 5-60 mg/mL of harvested sterilized collagen from Example 1. Bio gel compositions Q and R illustrate curable bio gel compositions, which include suitable cross-linking agents.

Example 3: Measurements of Rheological Properties for Bio Gel Composition

Figure 4:
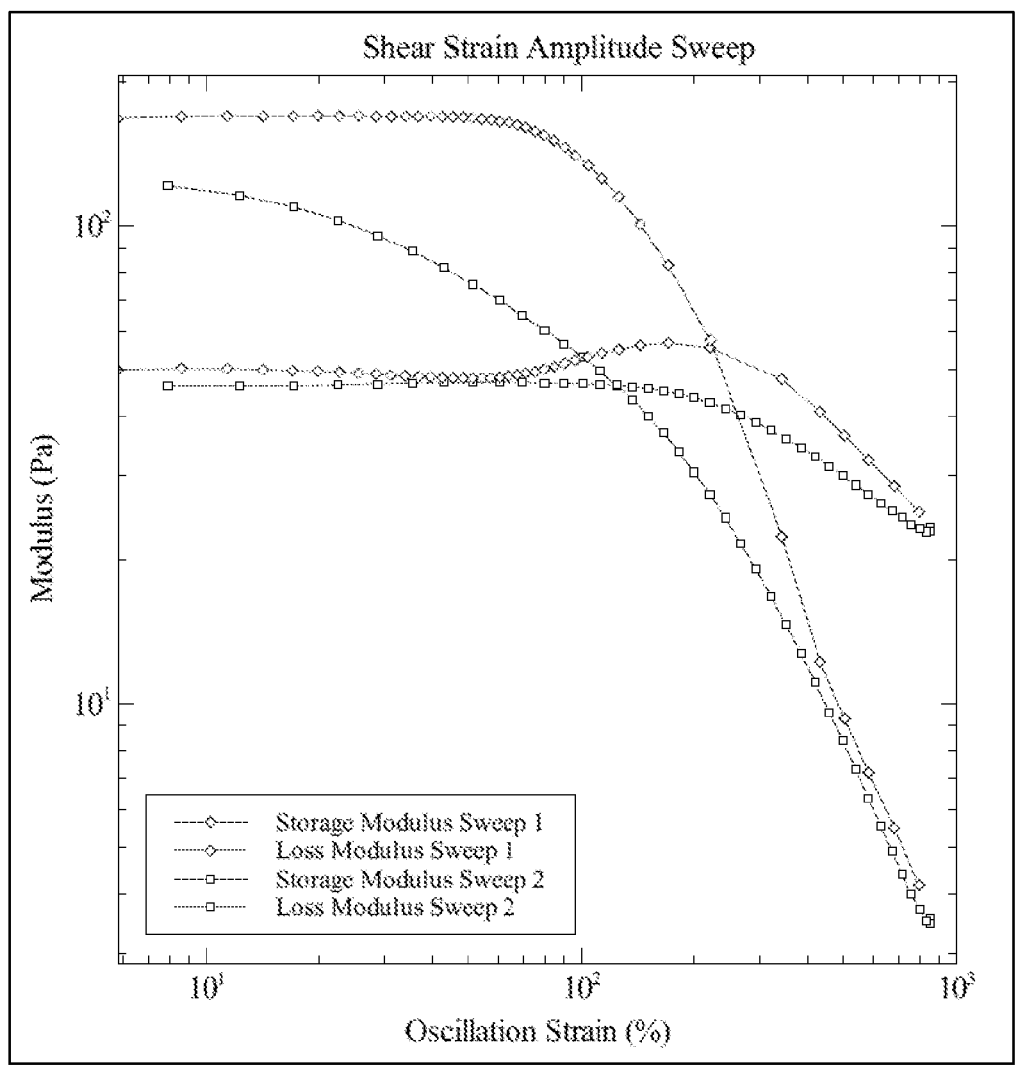
FIG. 4 is a graphical depiction of the non-Newtonian fluid behavior measurements for an uncured bio gel composition of the present technology.

This example illustrates the non-Newtonian fluid behavior for a sample acellular bio gel composition as described in Example 2. Rheological measurements were obtained using a TA Instruments Discovery Hybrid Rheometer (DHR-3), (40 mm parallel plate, Peltier steel plate; 1 mm gap). The sample plates were maintained between 2-6° C. The bio gel composition was deposited and spin coated onto the bottom sample plate and a top sample plate was used to cover the sample bio gel. Yield stress measurements were carried out on the deposited samples according to the following parameters:
Method:
Sweep 1—Oscillation Amplitude Ramp up
  Temp.: 0-12° C.
  Soak Time: 60 s
  Frequency: 1.0 Hz
  Linear sweep: 1.0 Pa to 200.0 Pa
Sweep 2—Oscillation Amplitude Ramp down
  Temp.: 0-12° C.
  Soak Time: 0 s
  Frequency: 1.0 Hz
  Linear sweep: 200.0 Pa to 1.0 Pa
Oscillation strain was plotted against modulus. FIG. 4 illustrates the intersection of storage and loss modulus for the sample bio gel, where the bio gel behaves as a liquid. For oscillation sweeps 1 and 2, the sample bio gel behaves as a liquid at a shear stress of 55 Pa and 47 Pa, respectively.

Example 4: Curing Properties Analysis of Bio Gel Compositions

Figure 5:
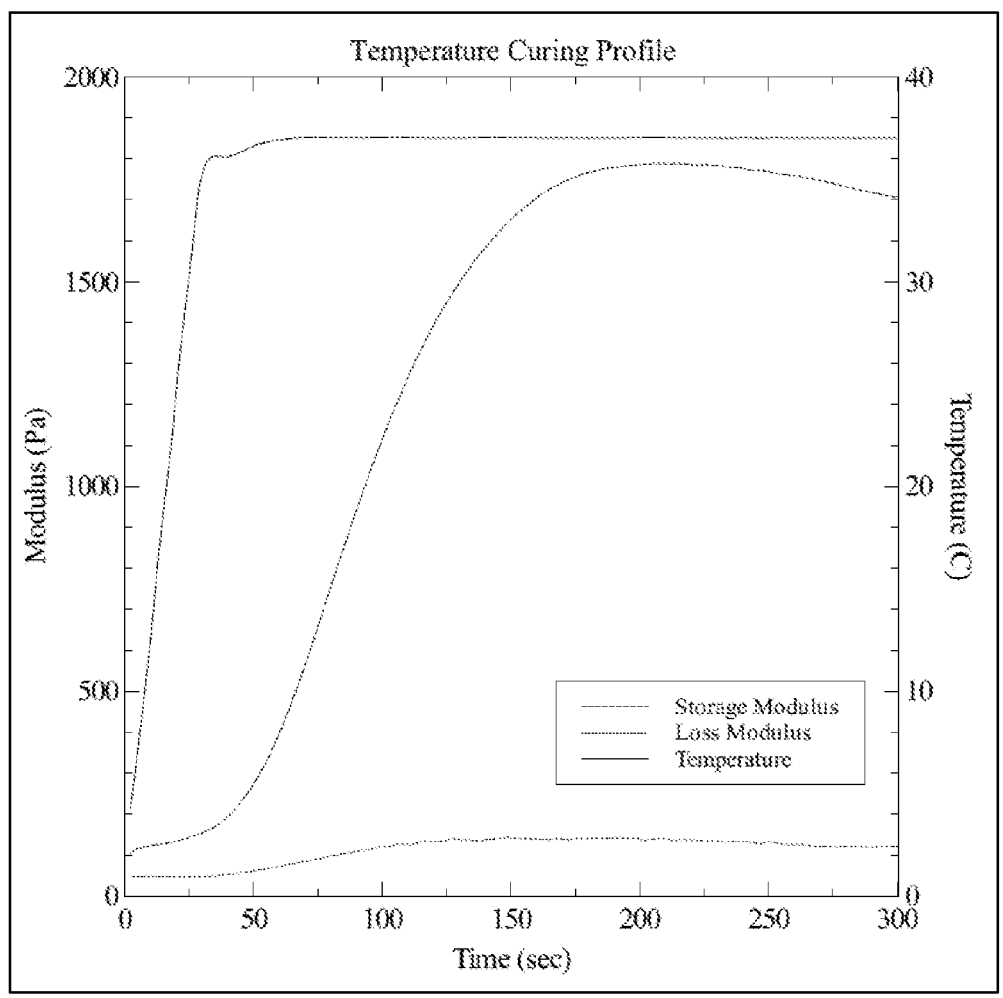
FIG. 5 is a graphical depiction of the storage and loss modulus profile during thermal curing for a bio gel composition of the present technology.
Figure 6A:
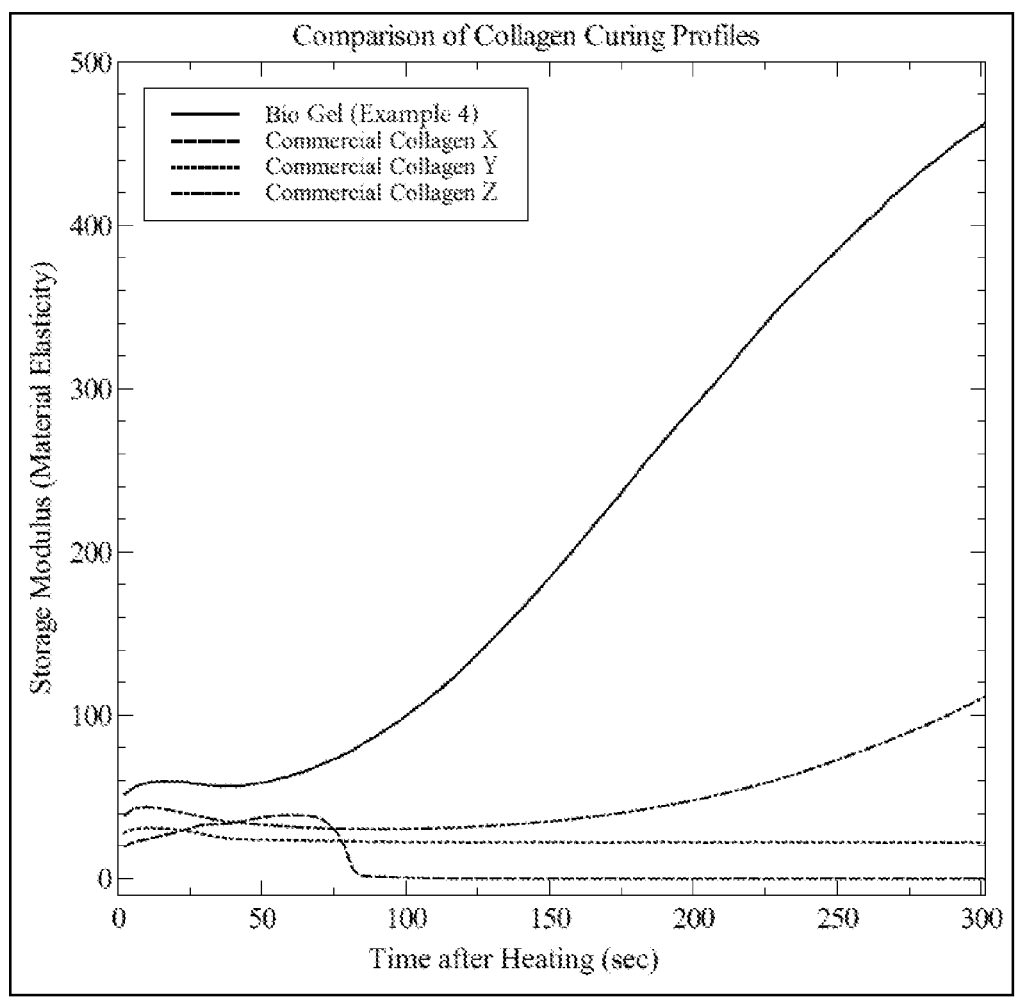
FIG. 6A is a graphical depiction of the increase in storage modulus of a bio gel composition of the present technology versus comparative commercial collagen bio gels.

This example illustrates the measurement of thermal curing properties of pre- and post-gelation bio gel compositions (Compositions A-J). Thermal curing measurements were obtained using a TA Instruments DHR-3 Rheometer (40 mm parallel plate, Peltier steel plate; 1 mm gap height). A sample bio gel composition was prepared as described in Example 2. An even coating of the sample bio gel was spin coated onto the bottom sample plate and a top sample plate was used to cover the coated bio gel.
Method:
Run 1 Oscillation Time:
  Temp.: 4° C.
  Soak Time: 0 s
  Frequency: 1.0 Hz
  Stress: 150 Pa
  Duration: 120 s
Run 2 Oscillation Time:
  Temp.: 37° C.
  Soak Time: 0 s
  Frequency: 1.0 Hz
  Stress: 10 Pa
  Duration: 300 s
FIG. 5 illustrates the rapid gelation and curing for the bio gel composition of the present technology, where the sample bio gel exhibited a 16-fold change in its storage modulus in less than 3 min. Curing measurements were also performed for bio gels prepared using commercial collagens according to the procedure described in Example 2 (FIG. 6A). The sample bio gel exhibited an over 6.5-fold increase in it storage modulus, while bio gels for commercial collagens X and Y exhibited no measurable increase and collagen Z exhibited a 1-fold increase.

Figure 6B:
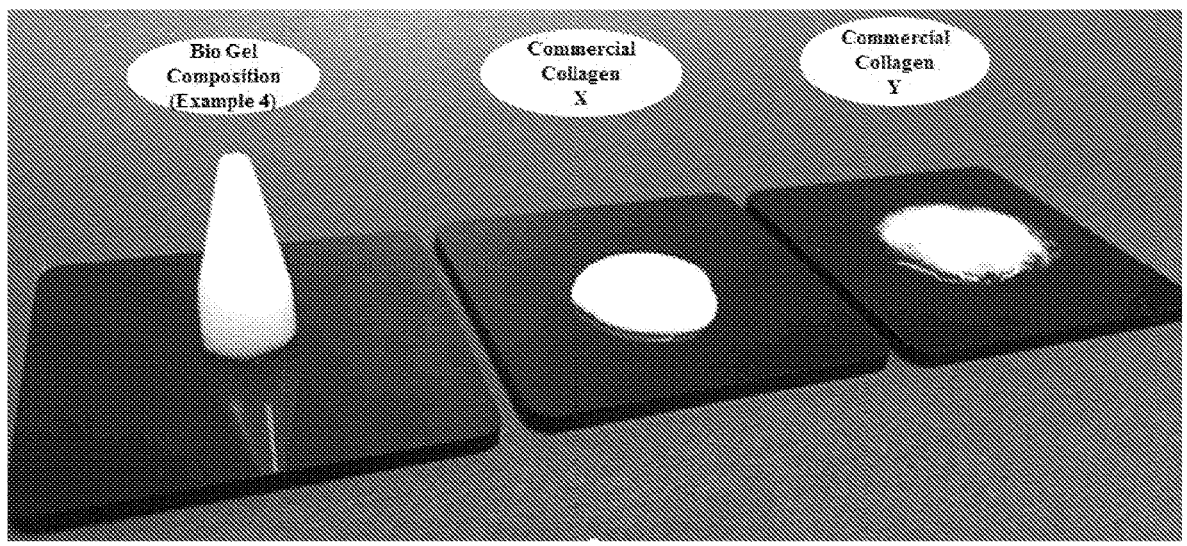
FIG. 6B are three-dimensional structure comparisons of a cured bio gel composition of the present technology compared to commercial collagen bio gels.

Cured and uncured bio gel compositions that include the collagen material (Example 1) and commercial collagens X and Y were prepared following the procedure in Example 2. Each sample was shaped into a 3D construct by injecting into a conical mold. The uncured sample bio gel remained solid under pressures up to 87 Pa, while the uncured 3D constructs containing commercial collagens failed to remain solid under pressures above 7 Pa (Commercial Collagen X) and 41 Pa (Commercial Collagen Y), respectively. The cured bio gel compositions were cured overnight in buffer. As evidenced by FIG. 6B, the cured three-dimensional structure of the sample bio gel of the present technology maintained its shape, whereas, the structures resulting from bio gel compositions using commercial collagens X and Y were unable to maintain a solid structure.

Example 5: Structural Stability Measurements of Three-Dimensional Structures

Figure 9:
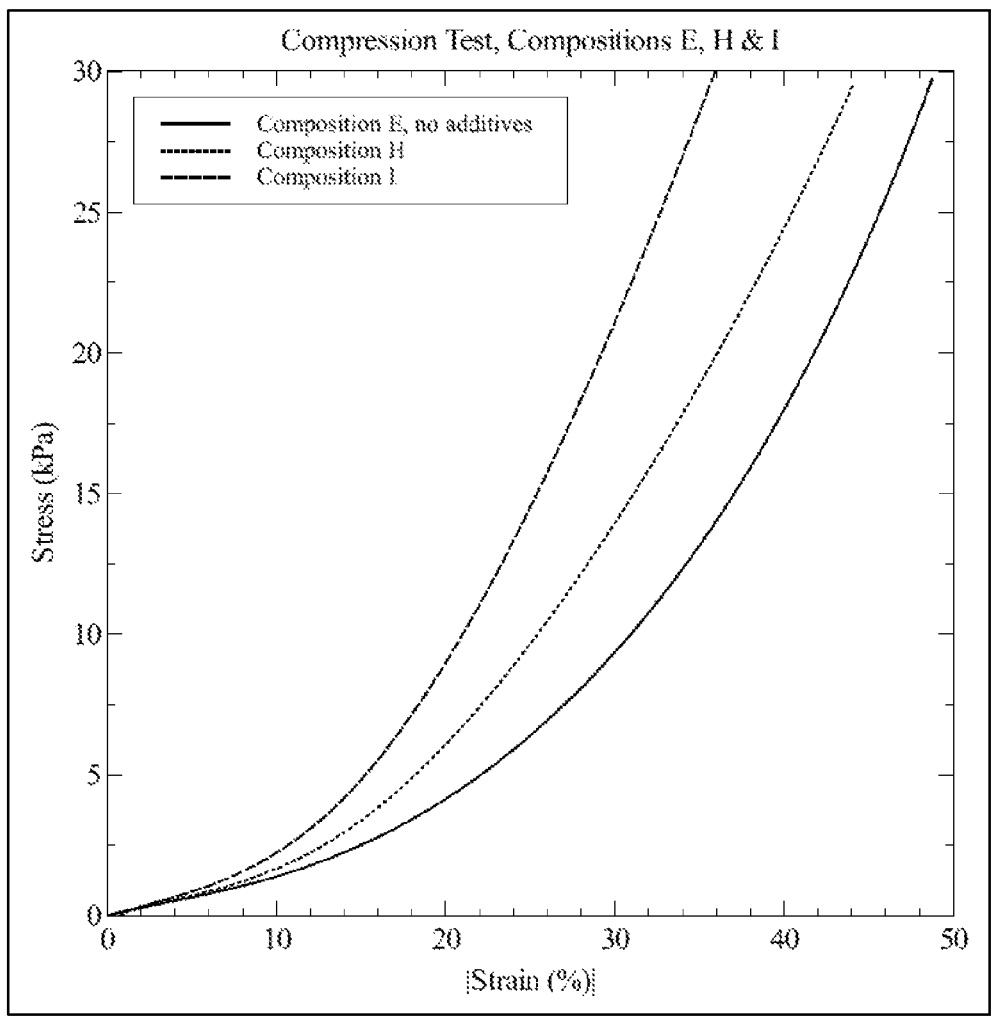
FIG. 9 is a graphical depiction of the compressive strength for cured three-dimensional structure of bio gel compositions with and without cross-linking agents.
Figure 10:
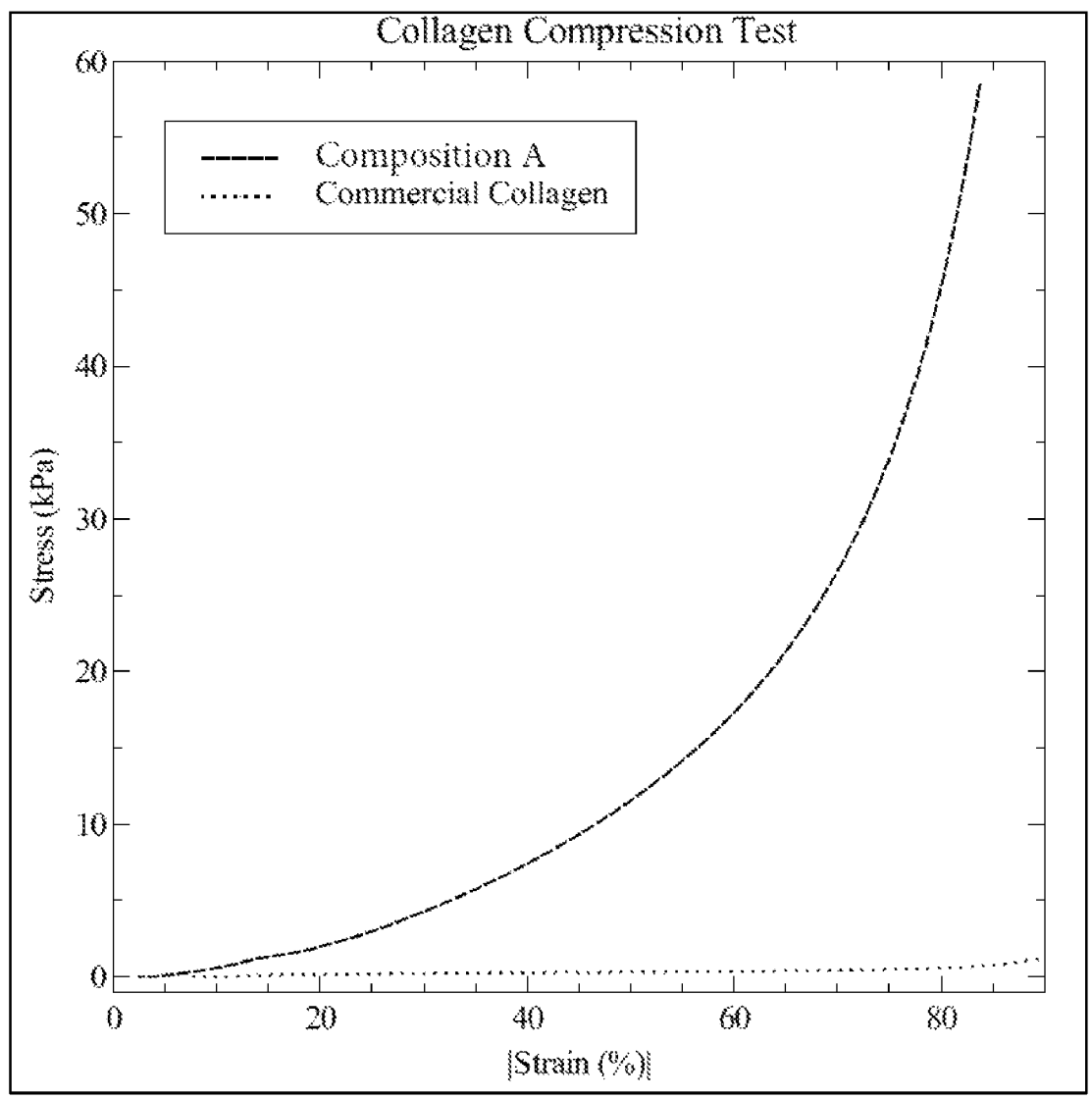
FIG. 10 is a graphical depiction of the a comparison of the compressive strength for cured three-dimensional structure of a bio gel composition of the present technology and a commercial collagen bio gel composition.

This example illustrates the structural stability measurements for cured three-dimensional structures formed from bio gel compositions as described in Example 2 and a bio gel containing commercial collagen. Dynamic mechanical analysis (DMA) for all samples was performed using a TA Instruments DMA Q800 Mechanical Thermal. Each sample was injected into round disk molds measuring approximately 5 mm in height and 10-14 mm in diameter. Cured bio gel samples were placed on sample plate of DMA Q800, and an initial height measurement was taken. The samples were maintained between 33° C. to 37° C. and allowed to soak for 3 min. Stress/strain plots were obtained at a ramp force of 1 N/min up to 3 N. Stress/strain plots for each of the tested exemplary compositions are provided in FIGS. 8 and 9. FIG. 10 provides a comparison of the structural stability measurements for a sample bio gel composition and a bio gel composition using a commercial collagen source (X).

Compositions H, I, and J were subjected to additional curing by exposing to a UV light source (Henry Schein-Maxima RU1200). Duration of exposure is dependent on size, construct, and distance of the UV light source.

Figure 7:
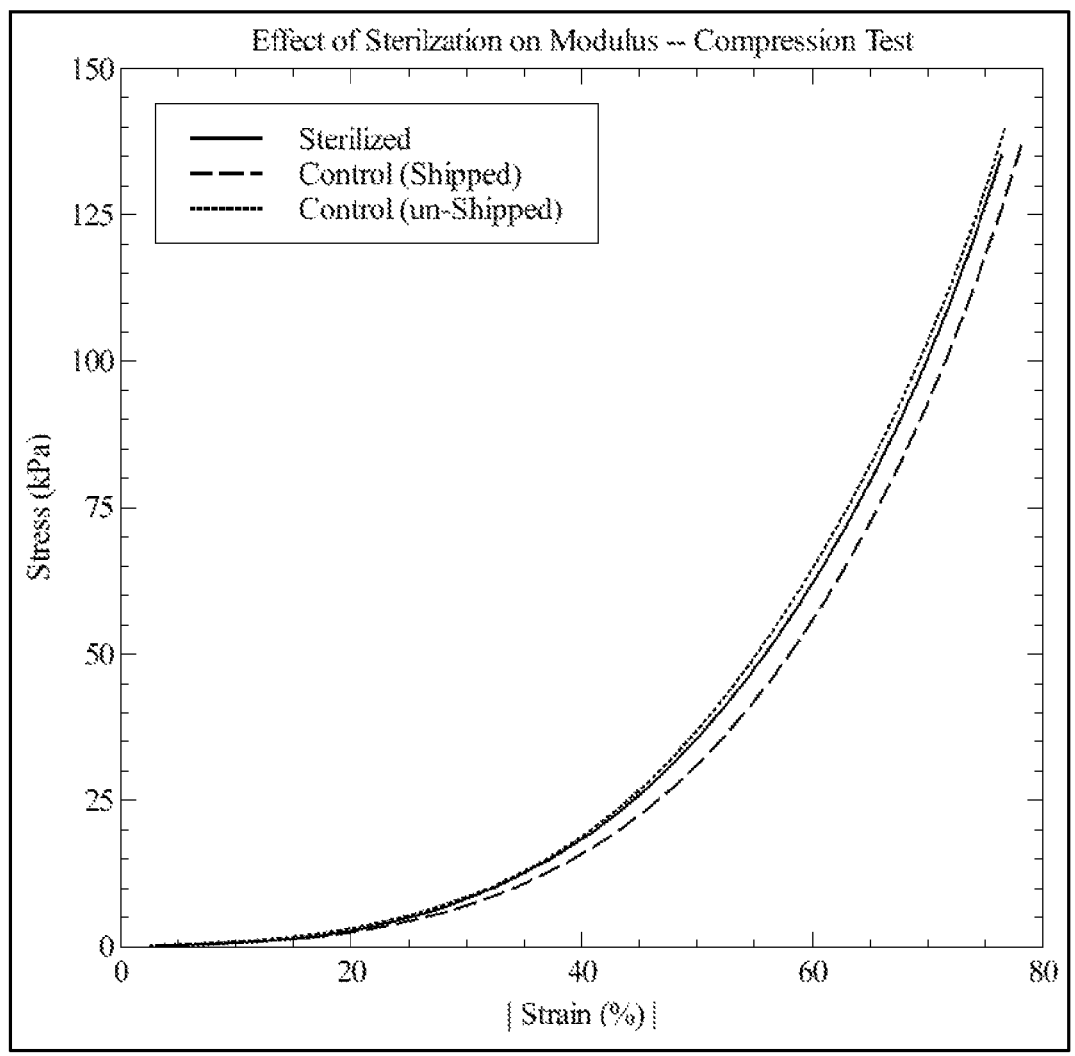
FIG. 7 is a graphical depiction of effects of peracid sterilization on modulus for collagen samples measured by unconfined compression test.
Figure 8:
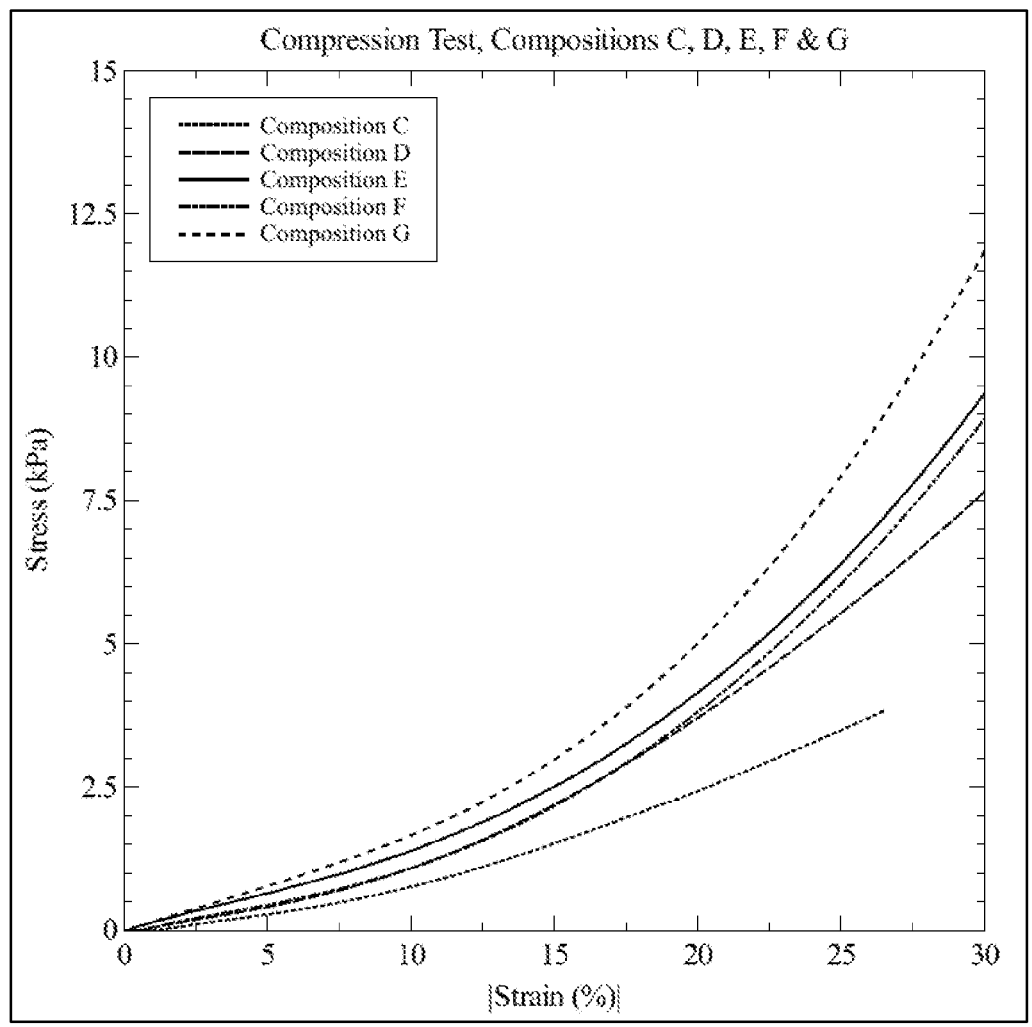
FIG. 8 is a graphical depiction of the compressive strength for cured three-dimensional structure of bio gel compositions of the present technology.

Measurements for Compositions A-J were plotted as a function of stress (kPa) versus strain (FIGS. 7 and 8 to provide the stress/strain ratios in Table 1). Each measurement was taken after thermal curing of Compositions A-J. It was observed that as the amount of harvested sterilized collagen in the bio gel composition increases, the stress/strain ratio also increases. FIG. 8 demonstrates that increasing the amount of collagen in the bio gel composition improves the compressive strength of the cured bio gel composition. Bio gel compositions that include ribose and riboflavin (Compositions H and I) were subjected to UV irradiation to initiate cross-linking. FIG. 9 demonstrates that bio gel compositions H and I exhibited higher stress/strain ratios than bio gel compositions free of cross-linking agents (Composition E).

Composition A exhibited a stress/strain ratio of 13.8 kPa, while bio gel compositions of commercial collagen (X) exhibited a stress/strain ratio of about 0.1 kPa. The results are summarized in Table 1 below:

TABLE 1

|  | †Stress/strain ratio, kPa |
|---|---|
| A, E | 13.8 |
| B | 7.1 |
| C | 8.5 |
| D | 11.4 |
| F | 11.1 |
| G | 16.8 |
| *H | 15.8 |
| *I | 25.3 |
| *J | 34.5 |

*Compositions were subjected to additional curing as described above.
†Slope calculated from 0-10% strain of plotted curve.

Example 6: Fabricating 3D Structure from Bio Gel Using 3D Printing Device

This example illustrates the method of fabricating a three dimensional structure with a 3D printing device using the bio gel compositions as described herein. A sample bio gel composition was prepared according to Example 2 and loaded into a syringe, where the syringe housing was maintained at 0° C. to 12° C. The syringe was connected to the printing device, and the bio gel composition was loaded into the printing device, which was temperature controlled at 0° C. to 12° C. The bio gel composition was extruded at a rate of 58 mm$^3$/s from the printing device and deposited onto a temperature controlled plate maintained between 25° C. to 37° C. An anatomical 3D structure was obtained. The anatomical 3D structure was cured in PBS from 34° C. to 37° C. overnight.

The above results illustrates the bio gel compositions of the present technology allow for high-fidelity 3D constructs that maintain their shape when formed, handled, and implanted. Furthermore, results illustrate the 3D constructs also have good compressive strength and elasticity, and desired textural and aesthetic properties.

While certain embodiments have been illustrated and described, a person with ordinary skill in the art, after reading the foregoing specification, can effect changes, substitutions of equivalents and other types of alterations to the present technology as set forth herein.

The present technology is also not to be limited in terms of the particular aspects described herein, which are intended as single illustrations of individual aspects of the present technology. Many modifications and variations of this present technology can be made without departing from its spirit and scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A bio gel composition comprising:
   collagen material in an amount greater than 5 mg/mL of the total bio gel composition;
   a weak acid solution;
   one or more cross-linking agents selected from ribose, riboflavin, and combinations thereof; and
   optionally living cells;
   wherein the bio gel composition:
      undergoes gelation in less than about 3 min at a temperature of about 25° C. to about 37° C.;
      is liquid under shear stress of about 15 Pa to about 100 Pa; and
      remains solid during gelation under hydrostatic pressure of about 30 Pa to about 120 Pa; and
   wherein the bio gel composition is obtained by a method comprising:
   providing a first receptacle having the collagen in the weak acid solution;
   providing a second receptacle having a carrier; and
   contacting the collagen material in the weak acid solution of the first receptacle with the carrier of the second receptacle to obtain the bio gel composition, wherein the contacting comprises stirring the collagen material in the weak acid solution and the carrier to form the bio gel composition until the bio gel composition has a homogeneity of about 50% to about 99.9%; and
   wherein the collagen material is obtained by a method comprising:
   (a) processing a collagen-based biomaterial to obtain biomaterial particles;
   (b) contacting the biomaterial particles with a weak acid solution to obtain a collagen-containing solution;
   (c) segregating the collagen-containing solution to obtain an extracted collagen solution;
   (d) contacting the extracted collagen solution with a salt solution to obtain a collagen precipitate;

(e) re-suspending the collagen precipitate in a weak acid solution to obtain a re-suspended collagen solution; and performing viral and prion inactivation of the re-suspended collagen solution;

(f) desalting the re-suspended collagen solution; and (g) drying the re-suspended collagen solution to obtain the collagen material.

2. The composition of claim 1, wherein the collagen material comprises type I collagen, wherein the type I collagen is harvested from mammalian sources selected from bovine, porcine, murine, or combinations thereof.

3. The composition of claim 1, wherein the collagen material is present in an amount of about 5 mg/mL to about 200 mg/mL.

4. The composition of claim 1, wherein the weak acid solution comprises weak acid in an amount of about 0.01% to about 3% of the weak acid solution.

5. The composition of claim 1, wherein the weak acid solution comprises formic acid, propanoic acid, acetic acid, citric acid, butanoic acid, salicylic acid, gluconic acid, heptonic acid, carbonic acid, hydrofluoric acid, nitrous acid, hypochlorous acid, or combinations thereof.

6. The composition of claim 1, wherein the bio gel composition sags less than about 1% to about 30% of its height under gravity over a period of up to about 60 s to about 120 s after gelation.

7. The composition of claim 1, wherein the bio gel composition increases storage modulus up to about 5000% after gelation.

8. The bio gel composition of claim 1, wherein the contacting comprises stirring the collagen material in the weak acid solution and the carrier to form the bio gel composition until the bio gel composition has a homogeneity of about 99.9%.

9. The composition of claim 1, wherein:
the method of obtaining the collagen material comprises contacting the biomaterial particles with the weak acid solution over a period of 24 h to 2 weeks; and
the segregating comprises centrifuging the collagen-containing solution.

10. The composition of claim 1, wherein contacting the extracted collagen solution with the salt solution is repeated until at least 95% pure collagen precipitate is obtained.

11. The composition of claim 1, wherein the method of obtaining the collagen material further comprises adjusting the pH of the re-suspended collagen solution to a pH of 2.8 to 4.5.

12. The composition of claim 1, wherein:
the desalting comprises dialysis against a 0.01% to 20% weak acid solution; and
the drying is carried out by supercritical fluid drying, cyclic pressure drying, inert medium drying, spray drying, fluidized bed drying, lyophilization, or dehydration.

13. The composition of claim 1, wherein the method of obtaining the collagen material further comprises, after (g):
(h) sterilizing the collagen material using irradiation, incubation with peracid, or supercritical fluid treatment.

14. The composition of claim 1, wherein the contacting comprises stirring the collagen material in the weak acid solution and the carrier to form the bio gel composition until the homogeneity of the bio gel composition is about 90%.

15. The composition of claim 1, wherein the collagen material is present in an amount of about 50 mg/mL to about 200 mg/mL of the total bio gel composition.

16. The composition of claim 1, wherein the collagen material is present in an amount of about 60 mg/mL to about 200 mg/mL of the total bio gel composition.

17. The composition of claim 1, wherein the collagen material is present in an amount of about 100 mg/mL to about 200 mg/mL of the total bio gel composition.

18. A method for fabricating the bio gel composition of claim 1 as a three-dimensional structure, comprising the steps of:
maintaining the bio gel composition at a temperature of about 0° C. to about 12° C.;
depositing the bio gel composition to form a three-dimensional structure, wherein the three-dimensional structure undergoes gelation; and
curing the three-dimensional structure.

19. The method of claim 18, wherein the three-dimensional structure undergoes gelation in less than about 3 min at a temperature of about 25° C. to about 37° C.

20. The method of claim 18, wherein the curing is performed at a temperature from about 34° C. to about 37° C. in a buffer solution.

* * * * *